(12) United States Patent
McDevitt et al.

(10) Patent No.: US 9,248,448 B2
(45) Date of Patent: Feb. 2, 2016

(54) MULTISAMPLE BIONANOCHIP PLATFORM

(71) Applicant: William Marsh Rice University, Houston, TX (US)

(72) Inventors: John McDevitt, Houston, TX (US); Nicolaos Christodoulidies, Houston, TX (US); Pierre N. Floriano, Houston, TX (US); Tim Abram, Houston, TX (US)

(73) Assignee: William Marsh Rice University, Houston, TX (US)

( * ) Notice: Subject to any disclaimer, the term of this patent is extended or adjusted under 35 U.S.C. 154(b) by 107 days.

(21) Appl. No.: 14/258,770

(22) Filed: Apr. 22, 2014

(65) Prior Publication Data

US 2014/0322103 A1  Oct. 30, 2014

Related U.S. Application Data

(60) Provisional application No. 61/815,305, filed on Apr. 24, 2013.

(51) Int. Cl.
| | | |
|---|---|---|
| *A61J 1/06* | (2006.01) | |
| *B01L 3/00* | (2006.01) | |
| *G01N 33/574* | (2006.01) | |

(52) U.S. Cl.
CPC ............. *B01L 3/5027* (2013.01); *B01L 3/5025* (2013.01); *B01L 2200/027* (2013.01); *B01L 2200/0605* (2013.01); *B01L 2300/069* (2013.01); *B01L 2300/0654* (2013.01); *B01L 2300/0681* (2013.01); *B01L 2300/087* (2013.01); *B01L 2300/0829* (2013.01); *B01L 2300/0874* (2013.01); *B01L 2300/0883* (2013.01); *B01L 2300/0887* (2013.01); *B01L 2400/0406* (2013.01); *B01L 2400/0683* (2013.01); *G01N 33/57407* (2013.01)

(58) Field of Classification Search
CPC .................. B01L 3/5027; G01N 33/57407
See application file for complete search history.

(56) References Cited

U.S. PATENT DOCUMENTS

| | | | |
|---|---|---|---|
| 7,316,899 | B2 | 1/2008 | McDevitt |
| 7,781,226 | B2 | 8/2010 | McDevitt |
| 8,101,431 | B2 | 1/2012 | McDevitt |
| 8,105,849 | B2 | 1/2012 | McDevitt |
| 8,377,398 | B2 | 2/2013 | McDevitt |
| 2004/0053322 | A1 | 3/2004 | McDevitt |
| 2005/0136548 | A1 | 6/2005 | McDevitt |
| 2006/0234209 | A1 | 10/2006 | Walker |

(Continued)

FOREIGN PATENT DOCUMENTS

| | | |
|---|---|---|
| WO | 2005090983 | 9/2005 |
| WO | 2007134189 | 11/2007 |

(Continued)

OTHER PUBLICATIONS

Weigum, S.E., et al., Cancer Prevention Research 2010, 3, 518-528.

(Continued)

*Primary Examiner* — Jyoti Nagpaul
(74) *Attorney, Agent, or Firm* — Boulware & Valoir

(57) ABSTRACT

A bionanochip cartridge for analysis of multiple samples or analytes is provided herein, and the cartridge is dimensioned to take advantage of existing robotic microtiter plate handling equipment. Fluidics are specially designed to provide a small footprint and to prevent cross contamination.

31 Claims, 16 Drawing Sheets

(56) References Cited

U.S. PATENT DOCUMENTS

| | | |
|---|---|---|
| 2006/0257854 A1 | 11/2006 | McDevitt |
| 2006/0257941 A1 | 11/2006 | McDevitt |
| 2006/0257991 A1 | 11/2006 | McDevitt |
| 2008/0038738 A1 | 2/2008 | Weigum |
| 2008/0050830 A1 | 2/2008 | Floriano |
| 2008/0176253 A1 | 7/2008 | Christodoulides |
| 2008/0219891 A1 | 9/2008 | McDevitt |
| 2008/0300798 A1 | 12/2008 | McDevitt |
| 2011/0251075 A1 | 10/2011 | McDevitt |
| 2012/0208715 A1 | 8/2012 | McDevitt |

FOREIGN PATENT DOCUMENTS

| | | |
|---|---|---|
| WO | 2007134191 | 11/2007 |
| WO | 2012065025 | 5/2012 |
| WO | 2012065117 | 5/2012 |

OTHER PUBLICATIONS

Weigum, S.E, et al., Lab on a Chip 2007, 7, 995-1003.
Weigum, S.E, et al., Oral Oncology 2009, 3, 111-111.

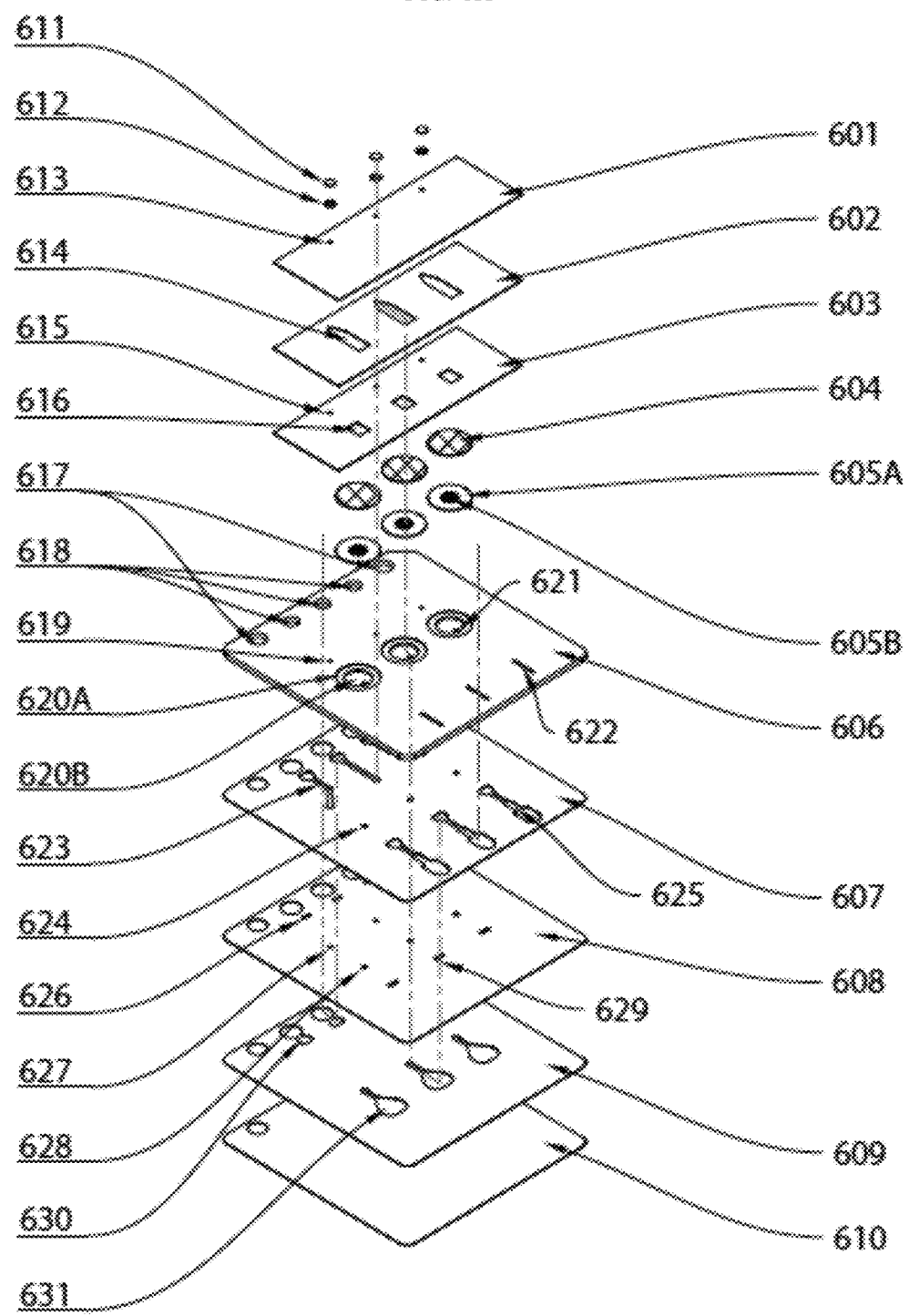

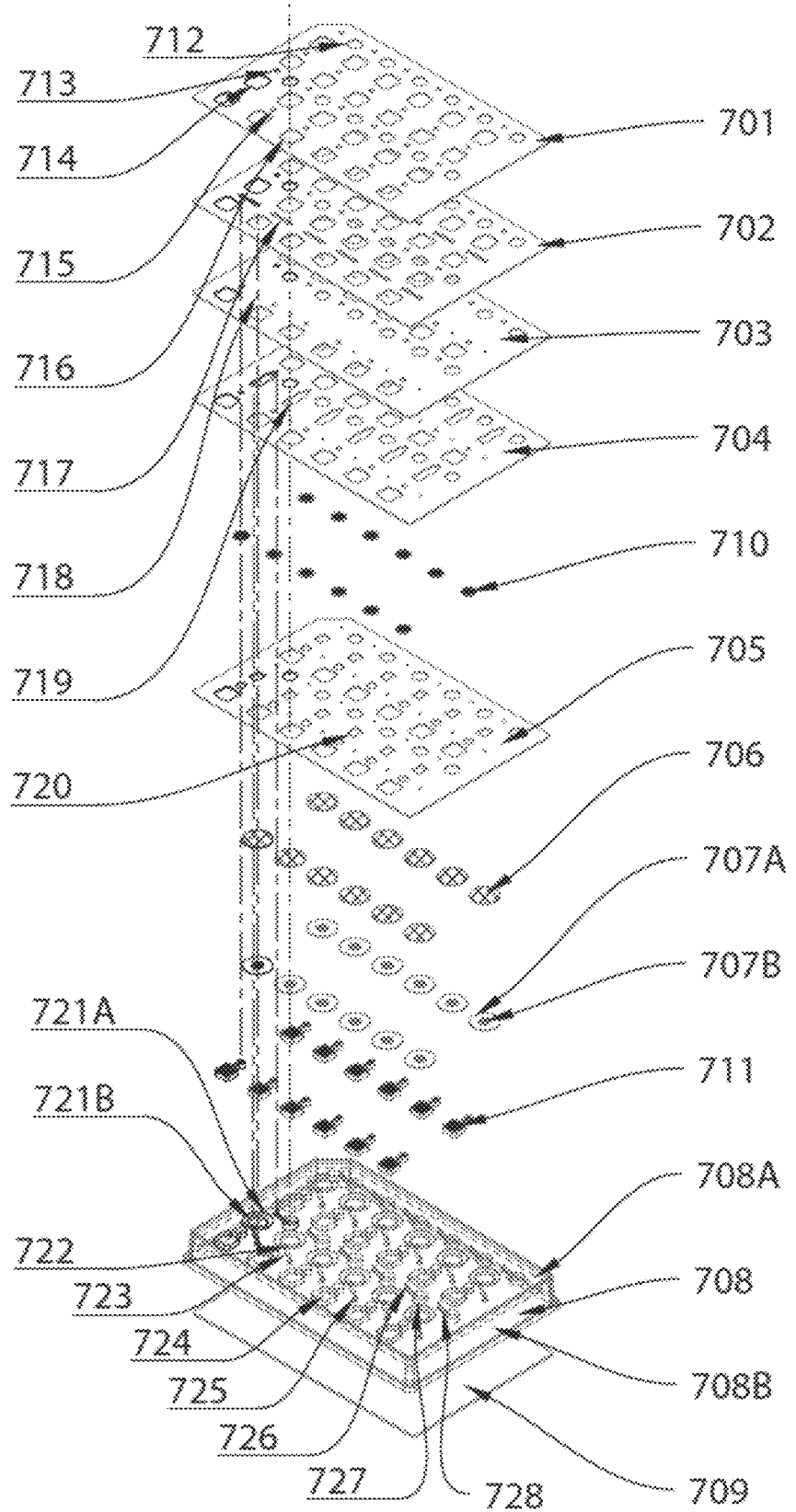

MULTISAMPLE BIONANOCHIP PLATFORM

PRIOR RELATED APPLICATIONS

This application claims priority to U.S. No. 61/815,305, filed Apr. 24, 2013 and incorporated by reference in its entirety for all purposes.

FEDERALLY SPONSORED RESEARCH STATEMENT

This invention was made with government support under Grant No: 1RC2-DE020785 and 3RC2-DE020785-02S1 awarded by the National Institutes of Health. The government has certain rights in the invention.

FIELD OF THE DISCLOSURE

The disclosure generally relates to platforms that employ the use of microtiter-sized cartridges for analysis of multiple samples and/or analytes at the same time, as well allow automated handling by virtue of employing a standard microplate footprint.

BACKGROUND OF THE DISCLOSURE

WO2012065025 and WO2012065117 describe bionanochip cartridges, system and software that allow the simultaneous quantification of cell morphometric data and expression of molecular biomarkers in an automated manner using refined image analysis algorithms based on pattern recognition techniques and advanced statistical methods. The device demonstrated at least 90% specificity and 90% sensitivity, preferably at least 92, 93, 94, 95, 96, or 97% specificity and sensitivity.

However, the cartridge therein only allowed the analysis of a single sample, and was limited in that multiple cartridges were required for multiple samples. This increases cost and time needed to either test a multiplicity of samples, or the same sample for a wider variety of analytes.

Therefore, there is a need in the art to provide devices that allow for the testing of a variety of samples and/or analytes in a single cartridge. A further benefit would be realized if the device could be handled by existing robotic fluid and sample handling equipment, thus allowing automation of analysis and increasing throughput. Yet a further benefit would be available if the device was easily manufactured from inexpensive components.

SUMMARY OF THE DISCLOSURE

This invention relates to a device that permits a greater number of samples to be analyzed according to the bionanochip method, i.e. for the assessment of morphological and molecular biomarkers because they are measured simultaneously in a parallel manner on a device that is characterized with outer dimensions of a microtiter plate, which has been modified to feature multiple repetitions of the membrane-based analysis chamber of the bionanochip.

Although the idea is simple in concept, it is actually quite difficult to realize in practice because there is a very limited footprint to work with on a standard microtiter plate. Further, the device incorporates numerous chambers for reactions and/or reagents and microfluidics are needed to effectuate the device. Thus, merely multiplying the existing device designs by six or 24 was impractical and specific modifications were required to allow multiple sample treatment chambers on a single device, prevent fluid loss, minimize cross contamination, leakage, and evaporation, allow optical access, allow for use of existing robotics, all the while providing simplified manufacturing of a robust and reliable device.

Such modifications include one or more of the following in any combination:

1) Top-Down Indirect Fluidic Pathway:

A top-down fluidic pathway in the disposable cartridge that initiates laterally to the reaction chamber and is indirect and thus longer than the straight, shortest pathway from the inlet to the reaction chamber—e.g., a fluid pathway from the top surface to the sample that includes at least one, two, three and preferably four changes in direction. Such a pathway is thus long enough to minimize the effects of fluid loss. Further, the laterally spaced inlet means that the chamber is still optically accessible from above and there is no optical interference from the walls of the fluidic pathway.

Preferably the inlets are at the same positions as the wells of a microtiter plate such that existing multi-pipettors can be employed in adding samples or reagents. The reaction chambers are thus slightly offset therefrom, providing each with a clear line of sight to any overhead magnifying lens and detectors, which can be chamber-by-chamber detection or full plate detection, depending on user available equipment, as both options are commercially available. Full plate detection is preferred as no adjustment would be needed for the offset reaction chambers.

The inlet, chamber, and outlet can each be laterally spaced from one another, so as to form a triangle from a top view. In an alternate preferred arrangement that conserves even more of the surface footprint, the chamber and outlet are stacked one on top of the other, adjacent a microtiter plate well position.

In preferred embodiments, the fluidic pathway can be S shaped, travelling down, across, then up to above the reaction chamber, then laterally to above the sample, and straight down through e.g., the edge of the reaction chamber (4 direction changes). The path can also travel down, across, up and laterally to the reaction chamber (3 changes). In other embodiments, the inlet fluids are shorter, travelling down from the inlet, laterally to above the sample, and then down through the reaction chamber (2 changes). In yet another, but less preferred embodiment, the inlet can travel down, then across to the reaction chamber (1 change). See FIGS. 1A-D for a simple schematic illustrating such fluid inlet pathways.

2) Passive Pumping:

While vacuum or active pumping means can be used, in a preferred embodiment, an optional passive pumping means is used. This can be e.g., an absorbent pad below and fluidly connected to the microfluidic channels in the disposable cartridge that will draw fluid through the device by capillary action once primed from above. The absorbent pad can be part of the disposable cartridge or a separate pad can be provided, but preferably the two are packaged as a single unit thus minimizing user implemented steps and handling. Where this embodiment is used, the outlets exit the bottom of the cartridge, directly on top of the pad, but otherwise, outlets could exit the side of the devices, though this is less preferred since gravity can aid in downward flow. In yet another embodiment, the outlets exit to the side to a vertically positioned/oriented pad.

3) Activatable Passive Pumping:

In a variation on the passive pumping theme, there is a layer of foil or some other water impermeable layer between the absorbent pad and the rest of the cartridge, and one inlet is sacrificed for use to penetrate the foil or an extra top down entry point can be provided for this. Thus, the user can incubate the reaction chamber for a period of time, then activate the pad pump by penetrating the foil, e.g., with a pipette tip or needle. Of course, automatic punching means can also be provided, but this may be less preferred where the device is designed to work with existing microtiter plate handling equipment, rather than dedicated cartridge-specific equipment.

4) Surface Treatments:

The action of the absorbent pad can be assisted by treating the surfaces of the microfluidic channels so as to make them hydrophilic, e.g., easily wettable. This will enhance the initial priming of the fluidics. One way to do this is by hydrophilic oxygen-plasma treatment of the basement layer of the inlet fluid channel. The surface treatment can include at least the fluid contacting surfaces, e.g., the inlets, outlets and chamber.

5) Dosing Manifold:

An optional dosing manifold is provided that sits above the disposable cartridge and allows the addition of the needed fluids to the sample cartridge in order to drive the various reactions. Of course, dedicated fluidic buses can be used instead, but the dosing manifold can have larger inlets and/or wells, allowing traditional robotics to apply fluids to the device and allowing capillary action to prime the microfluidics. In some embodiments, the dosing manifold is reusable, and reversibly couples with a disposable cartridge. In others, the dosing manifold is also disposable, and thus is packaged and provided a single unit with the remaining layers of the disposable cartridge.

The dosing manifold will include at least one inlet well for each reaction chamber, thus, allowing separate samples or reagents to be applied to each reaction chamber. The dosing manifold can also have a common well above the individual wells allowing application of a common fluid to the reaction chambers. Thus, a common fluid, e.g., a wash fluid can be applied to all of the reaction chambers after individual reactions are initiated with the individual inlets.

6) Framing Layer:

One or more of the layers can have an exterior surface that is the size (L×W, although H can vary) and shape of a microtiter plate, but have upper and/or lower pockets inside that serve to frame and hold the remaining layers in correct position. Thus, for example, a frit layer can have an upper pocket for layers above the frits, and a lower pocket into which all lower layers tightly fit, as well as pockets into which individual fits for each sample can fit (or a larger pocket for a single common frit). Alternatively, the dosing manifold can have an interior pocket or space on the underside into which the various layers of the cartridge can be inserted. The framing layer serves as a convenient way to both assemble the layers, and to provide a microtiter sized exterior footprint.

7) Optical Cover Layer:

An optically accessible cover layer is provided on top of the reaction chambers to prevent fluid loss by evaporation. This was typically a glass cover slip during prototype development, but any optically suitable material can be used, including glass, crystal, COC, COP, PMMA, thermoset ADC, and the like can be used. We have shown a glass cover used as the top-most layer, but this is for convenience of prototype development only, and a manufactured device could have a cover layer below the dosing manifold (with suitable holes for fluid entry) and thus be integral to the disposable cartridge. The cover can be conveniently placed close to the reaction chamber, such that the chambers can be fluid filled, eliminating any problem with vapor condensation on the underside of the cover.

The invention is currently exemplified with e.g., membrane or other porous material for capturing whole cells at the base of the reaction chamber and thus analyzing whole cell parameters, such as size, shape, surface antigens, and the like. However, the device could be easily adapted to other bionanochip platforms, i.e., an agarose bead-based platform for testing cell lysates with e.g., one or more agarose-bound antibodies, preferably monoclonal antibodies.

Additionally, we show a single membrane for all chambers, and have found there is no difficulty with contamination from one chamber to the other through the membrane, because we have exemplified the device using whole cells captured above the membrane, but in other assays it may be preferred to have separate membranes for each reaction chamber, and these can easily be provided in the same way that separate fits are fitted into pockets of the frit layer prepared to receive same.

While currently made as an assembly of layers that can be produced and stacked with adhesive materials, various welding and bonding techniques, clamps, screws, O-rings, or otherwise, the multi-assay device may alternatively be produced as only one or two pieces, through e.g., 3D printing, 3D laser etching, and the like. However, at this time injection molding is expected to be the most cost effective method of manufacturing the device in large quantities, and thus, at least 3 layers will be required (inlet layer, cover layer, chamber and outlet layer), plus a fourth absorbent pad layer (if used).

Although the prototypes were made with laser cutting each plastic and/or glass layer, the design is also compatible for production of some parts through injection molding of plastics. Further, by providing holes and etching on both the top and bottom of a given layer made by injection molding, we can reduce the number of layers needed. Additionally, the use of DSA and SSA layers may also be omitted if we employ other methods of affixing two layers together, such heat welding, RF welding, sonic welding, solvent welding, UV curable adhesive, hot embossing, heat staking, thermally fusing, and the like. Thus, the final commercial device is expected to have far fewer layers and to require no assembly by the user, beyond unpackaging it and inserting it into a robotic manifold, or possibly inserting it into a separate reusable dosing manifold/frame and then inserting the assembled part into the robotic manifold.

The prototypes were made of glass, single side adhesive vinyl, double side adhesives, polycarbonate membranes (0.4-3 micron pores), stainless steel frits, and the like, but these are exemplary only for the convenience of building laboratory prototypes. Other materials include but are not limited to glass, crystal, ceramics, resins such as polystyrene, polyacrylates, polypropylenes, polycyclo-olefins, etc. Resins are particularly preferred because they are inexpensive and it is relatively easy to prepare precision parts though high quality injection molding, and they allow a wide variety of welding and bonding techniques to bring multiple layers into sandwich formation.

Steel frits can be omitted, provided there is sufficient support otherwise, or replaced with porous ceramic frits, or even porous resins, such as are used in separation technologies. In particular, hollow fiber resins may be used as fits and to the extent that the fibers can all be vertically oriented, such that fluid doesn't travel laterally, it will be possible to use a common frit, rather than separate frits.

The outer dimensions and registration features of the device are identical to those of a microtiter plate—a well-established industry standard format—so it can be recognized and handled by most automation instruments and software. The manufacture of a 6 or 24 sample cartridge requires the use of the correct sized material, e.g., to fit a microtiter footprint of standard dimension, e.g.:

4.1.1 Footprint
4.1.1.1 The outside dimension of the base footprint, measured within 12.7 mm (0.5000 inches) of the outside corners, shall be as follows:
Length 127.76 mm±0.25 mm (5.0299 inches±0.0098 inches)
Width 85.48 mm±0.25 mm (3.3654 inches±0.0098 inches)
4.1.1.2 The outside dimension of the base footprint, measured at any point along the side, shall be as follows:
Length 127.76 mm±0.5 mm (5.0299 inches±0.0197 inches)
Width 85.48 mm±0.5 mm (3.3654 inches±0.0197 inches)
4.1.1.3 The footprint must be continuous and uninterrupted around the base of the plate.
4.1.2 Corner Radius
4.1.2.1 The four outside corners of the plate's bottom flange shall have a corner radius to the outside of 3.18±1.6 mm (0.1252 inches±0.0630 inches)

However, while a microtiter plate typically features open top wells with a base that function as reaction chambers, the multi-assay device features enclosed reaction chambers that are capped with an optical window with high transmission of light at wide range of wavelengths. Inlet wells with open bases and that are large enough for easy robotic filling are provided laterally to the reaction chambers, thus not obstructing view from above.

The multi-assay device can also feature reagent blisters, containing e.g., reagents or buffers, wash fluids, and the like. Space is limited, but reagent blisters could be provided at the sacrifice of one or more reaction chambers, or small reagent blisters may be compatible in the space between reaction chambers. See e.g., US20120322682.

The disposable multi-assay cartridges herein described can be used for any type of chemical or biological assay. One potential use is in the oral cancer application area for the efficient, high throughput parallel processing of exfoliated cellular samples from brush biopsy, consistent with operation processing samples from kits in centralized lab. Outside of the area of oral cancer, the same type of samples can be processed on this platform for screening, diagnostic, prognostic, and monitoring of various other diseases, whereby cellular samples can be available as in lung, esophageal, nasal, pharyngeal diseases and conditions. Other uses include the cellular screening of cells from various other samples such as blood, saliva, urine, lung lavages, sputum, nasal lavages, and the like for biomarkers, diagnostic metabolites and/or illicit drugs. Assay of water and other environmental samples for chemical or biological contaminants is another potential use.

The invention includes one or more of the following embodiments in any combination thereof:
A bionanochip cartridge comprising:
a) a substrate having an exterior footprint the width and length and shape of a standard microtiter plate;
b) said substrate having a 4×6 or 2×3 sample analysis arrangements therein, each sample analysis arrangement having:
  i) a top loading inlet port fluidly connected to a reaction chamber that is laterally spaced from said inlet port;
  ii) an indirect fluid pathway connecting said inlet port and said reaction chamber;
  iii) said reaction chamber having a transparent cover overhead allowing visual inspection of said reaction chamber from overhead;
  iv) said reaction chamber having a porous base;
  v) said reaction chamber fluidly connected under said porous base to an outlet port.

A bionanochip cartridge comprising:
c) a substrate made of layers held in leak proof juxtaposition and having an exterior footprint the width and length and shape of a standard microtiter plate;
d) said substrate having a 4×6 or 2×3 sample analysis arrangements therein, each sample analysis arrangement having:
  i) a top loading inlet port fluidly connected to a reaction chamber that is laterally spaced from said inlet port;
  ii) an indirect fluidic pathway having at least 2 changes of direction connecting said inlet port and said reaction chamber;
  iii) said reaction chamber having a transparent cover overhead allowing visual inspection of said reaction chamber from overhead;
  iv) said reaction chamber having a porous base;
  v) said porous base fluidly connected to a outlet port;
  vi) an absorbent pad below said outlet port.

A bionanochip cartridge having an indirect fluidic pathway with 4, 3, 2 or 1 changes of direction before reaching said reaction chamber.

A bionanochip cartridge having an indirect fluidic pathway that begins at a top of said cartridge, proceeds to below said reaction chamber, then laterally, then to above said reaction chamber, then laterally, and then down to said reaction chamber.

A bionanochip cartridge comprising a plurality of outlet pathways beneath said membrane, said outlet pathways fluidly connected to said outlet port.

A bionanochip cartridge having a porous base that comprises a membrane or a membrane and a porous frit beneath said membrane.

A bionanochip cartridge wherein said fluidic pathway has a hydrophilic fluid contacting surface, preferably the entirety of said fluidic pathway is hydrophilic.

A bionanochip cartridge comprising an absorbent pad below said substrate and fluidly connected to said outlet port.

A bionanochip cartridge comprising an impermeable layer above a bottom layer comprising an absorbent material and wherein a hole is provided through said bionanochip cartridge such a that a user can penetrate said impermeable layer through said hole.

A bionanochip cartridge wherein said outlet port is directly below said reaction chamber.

A bionanochip cartridge wherein said substrate is comprised of at least a transparent cover layer over an inlet layer over a reaction chamber layer over an outlet layer, each of said layers affixed to an adjacent layer in a fluid tight manner.

A bionanochip cartridge wherein said substrate is comprised of at least an inlet layer over a transparent cover layer over a reaction chamber layer over an outlet layer, each of said layers affixed to an adjacent layer in a fluid tight manner, or at least an inlet layer, a transparent cover layer, a reaction chamber layer, and an outlet layer, each of said layers affixed to an adjacent layer in a fluid tight manner.

A bionanochip cartridge wherein said transparent cover layer is an uppermost layer or an interior (intermediate) layer.

A bionanochip cartridge wherein at least one of said layer contains at least one pocket on a top or bottom surface thereof for tightly receiving additional layers.

A bionanochip cartridge wherein an uppermost layer has an exterior size and shape of a microtiter plate and has a pocket on a bottom surface thereof for tightly holding additional layers, or wherein a middle layer has an exterior the size and shape of a microtiter plate and has pockets on a bottom surface thereof and a top surface thereof for tightly holding additional layers.

A bionanochip cartridge wherein a middle layer has one or more pockets to receive one or more frits.

A bionanochip cartridge having a bottom layer comprising an absorbent material, preferably an absorbent material sized to absorb all fluid from a given multi-assay.

A bionanochip cartridge further comprising a plurality of outlet pathways beneath said membrane, said outlet pathways fluidly connected to said outlet port.

A bionanochip cartridge having a porous base comprising a membrane for catching cells, preferably a membrane for catching cells with a fit thereunder, or an agarose pad or bead, the agarose preferably having one or more antibodies conjugated thereto.

A bionanochip framing device having external dimensions of a standard microtiter plate and at least one interior pocket on an upper or lower surface thereof, said interior pocket for receiving an assay cartridge, said framing device also having a plurality of holes traversing from said upper surface to said lower surface.

A bionanochip framing device having an upper interior pocket and a lower interior pocket or just a lower interior pocket.

A bionanochip framing device having 2×3 or 4×6 arrangement of open bottom wells.

A bionanochip framing device having 2×3 or 4×6 arrangement of open bottom wells in the location of wells in a standard microtiter plate.

The terms "cartridge" or "card" is used herein to describe the multi-assay devices described herein, each having multiple reaction chambers such that assays can be run in parallel, and having the external dimensions of a microtiter plate. Preferably, such devices are single use disposables.

The term "sandwich" as used herein refers to two or more layers that are placed in juxtaposition, such that fluids can travel therethrough without leakage. Preferably, the layers are affixed to one another, by the various welding, bonding and other methods mentioned herein, but this is not essential and they could be clamped together in a fluid tight manner.

The term "framing layer" or "framing device" refers to a layer having the external dimensions of a microtiter plate, but having upper and/or lower pockets into which the other sandwiched layers will fit, thus giving the entire cartridge the correct exterior dimension. The framing layer can be integral with a disposable cartridge, or a separate reusable element.

The term "dosing manifold" refers to an upper layer with wells and inlets at the bottom of each well leading to the inlets on the assay cartridge. Preferably the wells of the dosing manifold are in the same position as wells on microtiter plate. A dosing manifold and framing layer can be combined into a single layer serving both functions.

By "reflecting" the arrangement of wells what is meant is that the arrangement of sample analysis locations mirrors the arrangement of wells in a standard microtiter plate sufficiently as to allow standard multi-pipettors and robotics for same to deliver fluids to the device, although one or more locations may be sacrificed for other needs, e.g., blister packs, needle punch site, etc. Such plates typically are available in 6, 12, 24, 48, 96 etc. sizes.

The word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, and the like.

The word "morphometric" as used herein means the measurement of such cellular shape or morphological characteristics as cell shape, size, nuclear to cytoplasm ratio, membrane to volume ratio, and the like.

The following abbreviations are used herein:

| ABBREVIATION | TERM |
|---|---|
| Ab | antibody |
| ADC | allyl diglycol carbonate |
| BNC | bionanochip |
| CNC | Computer numerical controlled |
| COC | Cyclo-Olefin Copolymer |
| COP | Cyclo-Olefin Polymer |
| DSA | Double side adhesive |
| MAb | Monoclonal antibodies |
| MAD | Multi Assay Device |
| p-BNC | Programmable bionanochip |
| PCP | Primary Care Physician |
| PET | Polyethylene terephthalate |
| PMMA | Poly(methyl methacrylate) |
| SAD | Single Assay Device |
| SSA | Single side adhesive |

BRIEF DESCRIPTION OF THE DRAWINGS

FIG. 2A shows an exploded view of an 8 layer prototype, wherein both inlet and outlets are accessible from an upper surface and wherein the fluidic pathway is shown by the dashed line. FIG. 2B shows a top view of the same device. FIG. 2C shows a cross sectional view of the reaction chamber through the center of the device at line C-C.

FIG. 3A shows an exploded view; FIG. 3B shows a top view; and, FIG. 3C shows a cross section of layer 305 through line C-C, clearly illustrating the underpocket and overpocket into which the other layers can be fitted.

FIG. 5A is an exploded view; FIG. 5B is a top view; and, FIG. 5C a cross section through line C-C. FIG. 5D shows a close up of a corner chamber (circle D) of the same cross sectional view through line C-C. FIG. 5E shows a transparent perspective view.

FIG. 6A-C shows a MAD-3 device wherein FIG. 6A is an exploded view; 6B a top view; and, 6C a cross sectional view through line C-C.

FIG. 7A-G shows an automated, passive fluid pumping scheme in a 12-analyte device (MAD-12) wherein FIG. 7A is an exploded view; 7B a top view; and, 7C a cross sectional view through line C-C. FIG. 7D shows a top view of the assembled device wherein the circle locates the blow up view in FIG. 7E. FIG. 7F a top view; and, FIG. 7G is a cut out view through line G-G.

DETAILED DESCRIPTION

Figure 1A:
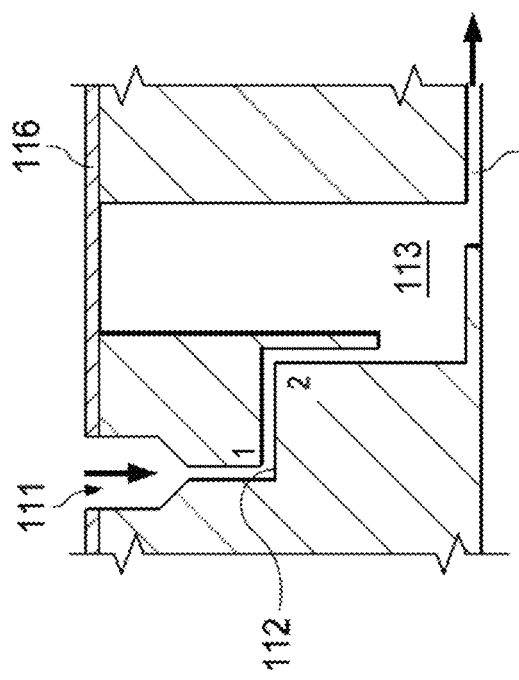
FIG. 1A-D show a cross section of a portion of a multi-assay device indicating the indirect microfluidic pathways have 4 changes of direction (FIG. 1A), 3 changes of direction (FIG. 1B), 2 changes of direction (FIG. 1C), and one change of direction (FIG. 1D).
Figure 1C:
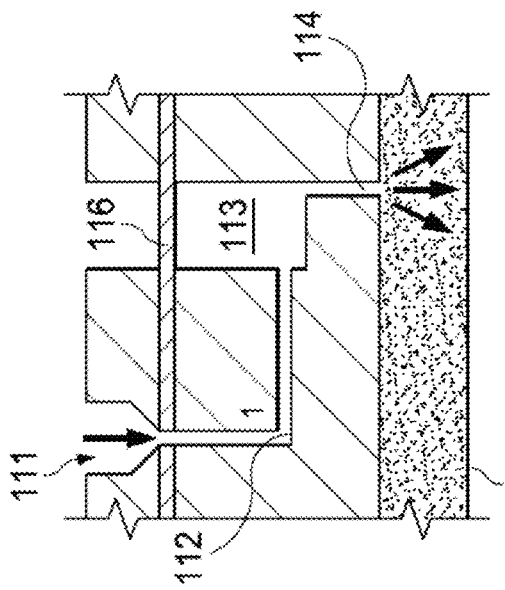

The disclosure provides multi-sample cartridges for use in high throughput assays using microtiter plate handling equipment. There are several issues that need to be addressed to manufacture an inexpensive and reliable, disposable, microtiter-sized device for assaying more than one microliter sized sample in parallel. First, since samples are very small, evaporation must be minimized. Therefore, a cover is needed to prevent or minimize evaporation. However, one still needs a means of introducing fluid, therefore, some inlet must be provided. Second space is at a premium, thus, top down fluidics (or vice versa) will provide the best use of space, together with top down sample visualization. Yet, the need for a cover impacts visualization. At the same time, the device must be constructed to as to minimize leakage, and optimize fluid flow through the sample. All of these issues become even more difficult to solve as the sample multiplicity is increased and available size thus decreases. Further, the smaller the device, and, especially when combined with a membrane for cell trapping, fluid flow becomes a limiting issue.

In general, we have solved these issues by providing a long inlet pathway laterally spaced from the sample analysis location, which can then be visualized from the top. Some of the designs show an S shaped fluidic pathway, where fluid travels down from a top or side surface inlet to below the sample well (membrane), then up to a larger chamber which allows the fluid to flow laterally, then down though the sample membrane. This is only one option, however, and the fluids need not travel all the way below the membrane, but can travel to a lesser depth. In yet another option, the sample can be top loaded, travel down a very short amount, travel laterally, then down through the sample. However, as array density increases, space becomes very limited, and the longer up/down pathway both conserves surface space and provides considerably protection against fluid loss, any loss affecting only excess fluid in the fluidic pathway, not fluid in the actual sample. The point being that having a significant fluidic pathway with small inlet that is upstream of the sample will protect the sample from fluidic loss.

Fluid outlets are at the side or preferably bottom surface of the cartridge, as this minimizes surface footprint and also allows gravity to assist with drainage. In particularly preferred embodiments, the outlets are directly below the reaction chambers.

Another focus of our work was to free the device from its dependency on active pumping equipment in order to easily scale up the number of assays that can occur simultaneously. Various modes of passive pumping were explored, namely capillary action through changes in surface energy, hydrostatic pressure-driven flow, electro wetting, capillary-driven laminar flow via an absorbent pad sink, and combinations thereof.

The fluidic resistance imposed by the cell-capturing membrane creates many challenges for traditional pump-less solutions. The most effective combination of passive fluid delivery modes was discovered to be a capillary-driven "priming" step by hydrophilic oxygen-plasma treatment of the basement layer of the inlet fluid channel coupled with an absorbent pad outlet sink, whose pressure differential creates a strong driving force comparable to active pumping. The surface area of the absorbent is proportional to the total liquid volume required of the individual assay in order to maintain a constant flow rate through the course of the assay.

Another focus was to eliminate dedicated fluid buses allowing for fluidic entry, as such equipment is complex, subject to leakages and hinders throughput. Instead, we investigated options that would allow robotic multi-pipettors to be used with a standard microtiter plate.

Several concepts for a "dosing manifold" were explored. The primary concept assumes that the assays are performed in a disposable card that includes layers encompassing various fluid channels and a cell-capture membrane that interfaces with a reusable dosing manifold that is designed to leverage the standardized dimensions of a traditional multi-well plate. Once assembled, the assays may be performed manually through the addition of reagents to the separate wells via a multi-channel pipette, or automatically through the use of robotic liquid handlers. The overall goal is to fully automate these assays by making the interfacial design compatible with robotic liquid handlers, pick-and-place equipment, and automated imaging stages and subsequent data processing.

Prototype dosing manifolds may not possess the fully-automated characteristics desired in the final device. Some, for example may include the use of threaded fasteners such as thumb-screws or external clamps. Other prototype manifolds may lack the card holding function, which is separately provided by a separate framing layer, e.g., a bottom piece into which the sandwich cartridge is fitted, then the top dosing piece is clamped to by the use of external fasteners.

Figure 5A:
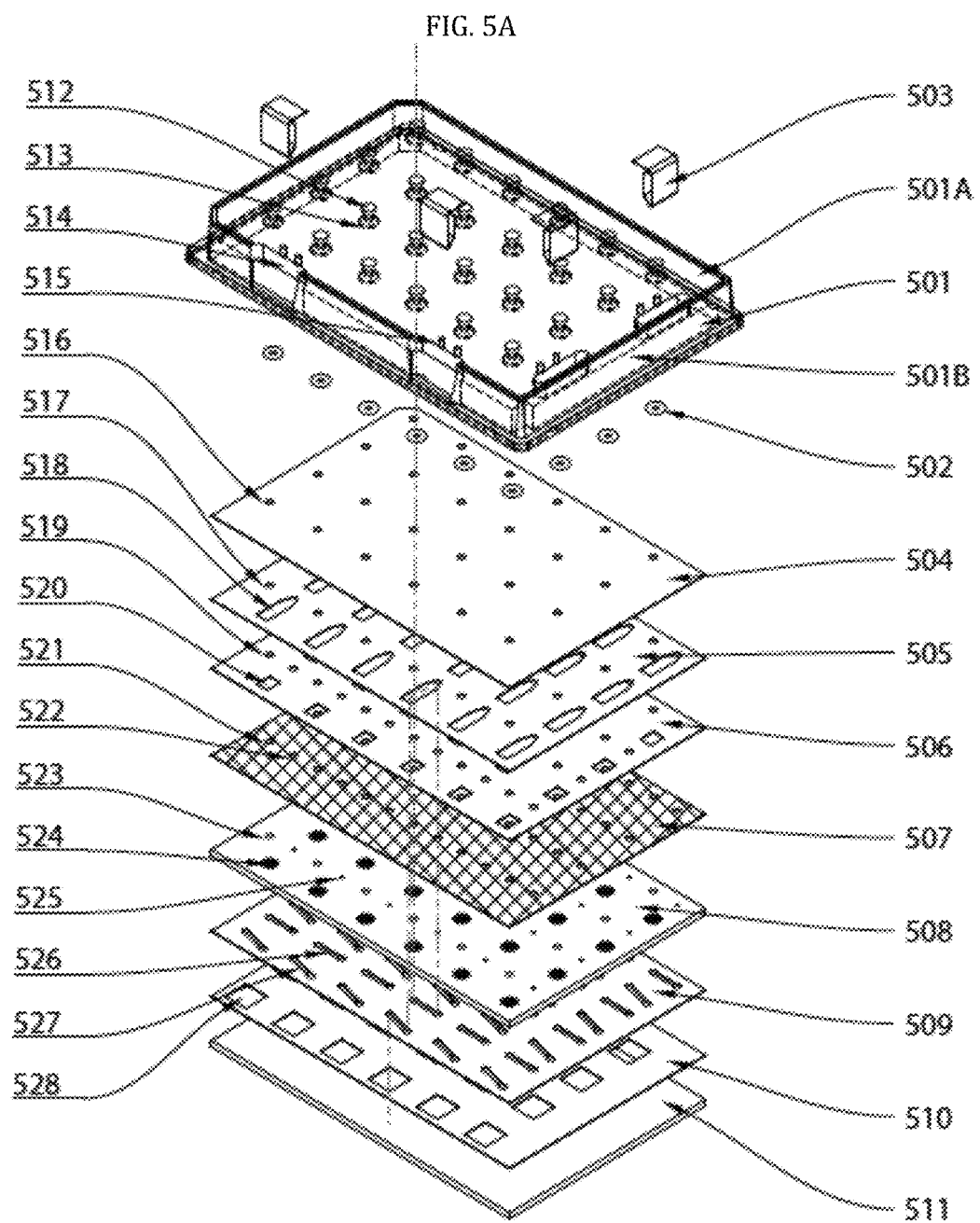
FIG. 5A-E show a prototype MAD-24 device with a dosing manifold having an underpocket to hold the remaining sandwich layers. This prototype is held together with snap on clamps, but a final device will likely contain snap fit projections and or protrusions in the pocket to snap fit to the sandwich or other integral fastening means.

A combined manifold and framing layer design, as in FIG. 5A, however, operates as a complete unit having upper inlets and an internal pocket on the underside into which the card fits. The device in FIG. 5A shows added clamps, but in a commercial embodiment will have internal fasteners or a snap fit design can be used wherein the lower sandwich layers have one or more protrusions that snap fit into one or more recessions (or vice versa) provided in a pocket shaped to receive the sandwich, thus eliminating any clamps, screws or other fasteners.

The dosing manifold and assay card assembly are designed to allow the multiple assays to be performed via simple reagent addition in a desired sequence to the generously sized inlet well in the dosing manifold. Once the channels and membrane are "primed" by the addition of a buffer that travels via surface-tension capillary action toward the absorbent pad at the outlet, capillary-driven flow commences utilizing the absorbent pad as a sink. The remaining cell suspension and staining reagents are added sequentially to the same inlet in desired volumes at defined time points. These steps can be automated for use with a robotic liquid handler or can be performed manually. Once the final wash step is completed, the assay card can be removed from the dosing manifold assembly and can then undergo imaging of the assay regions. Alternatively, in a high through put environment, the lens and CCD camera or CMOS imager can swing into position over the unit.

Figure 1B:
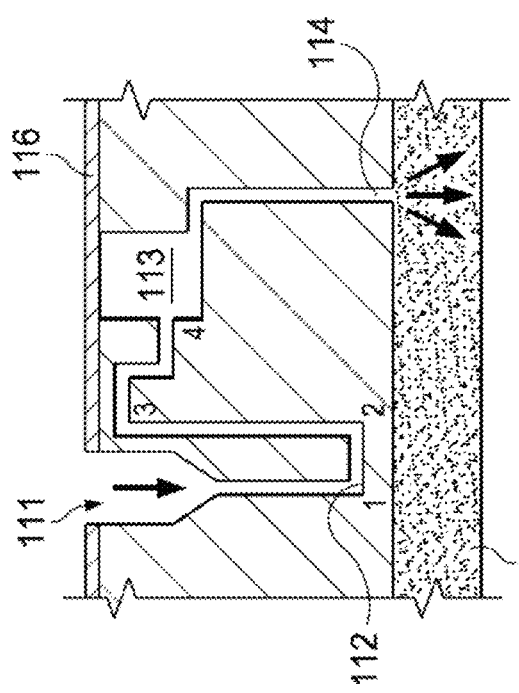
Figure 1D:
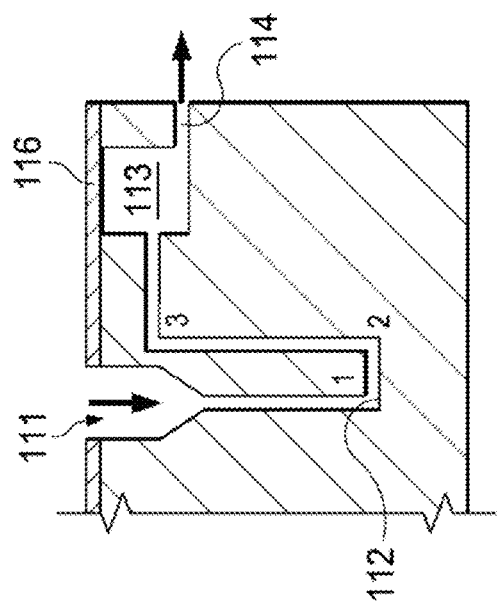

FIG. 1A-D show various implementations of a top-down indirect fluidic pathway having 4 (1A), 3 (1B), 2 (1C) and 1 (1D) changes in direction. In FIGS. 1B and C, fluid outlets are at the side, and in FIG. 1A, D the outlets are at the bottom. Throughout FIG. 1A-D, 111 is the fluid entry port/chamber, 112 is the fluidic pathway with 1-4 changes of direction, 113 is the reaction chamber, while 114 is the fluid outlet. The absorbent pad is 115 and provides passive pumping for the fluid. The optically transparent cover layer 116, can be an uppermost or interior layer, as desired depending on reaction chamber size and depth.

Figure 2A:
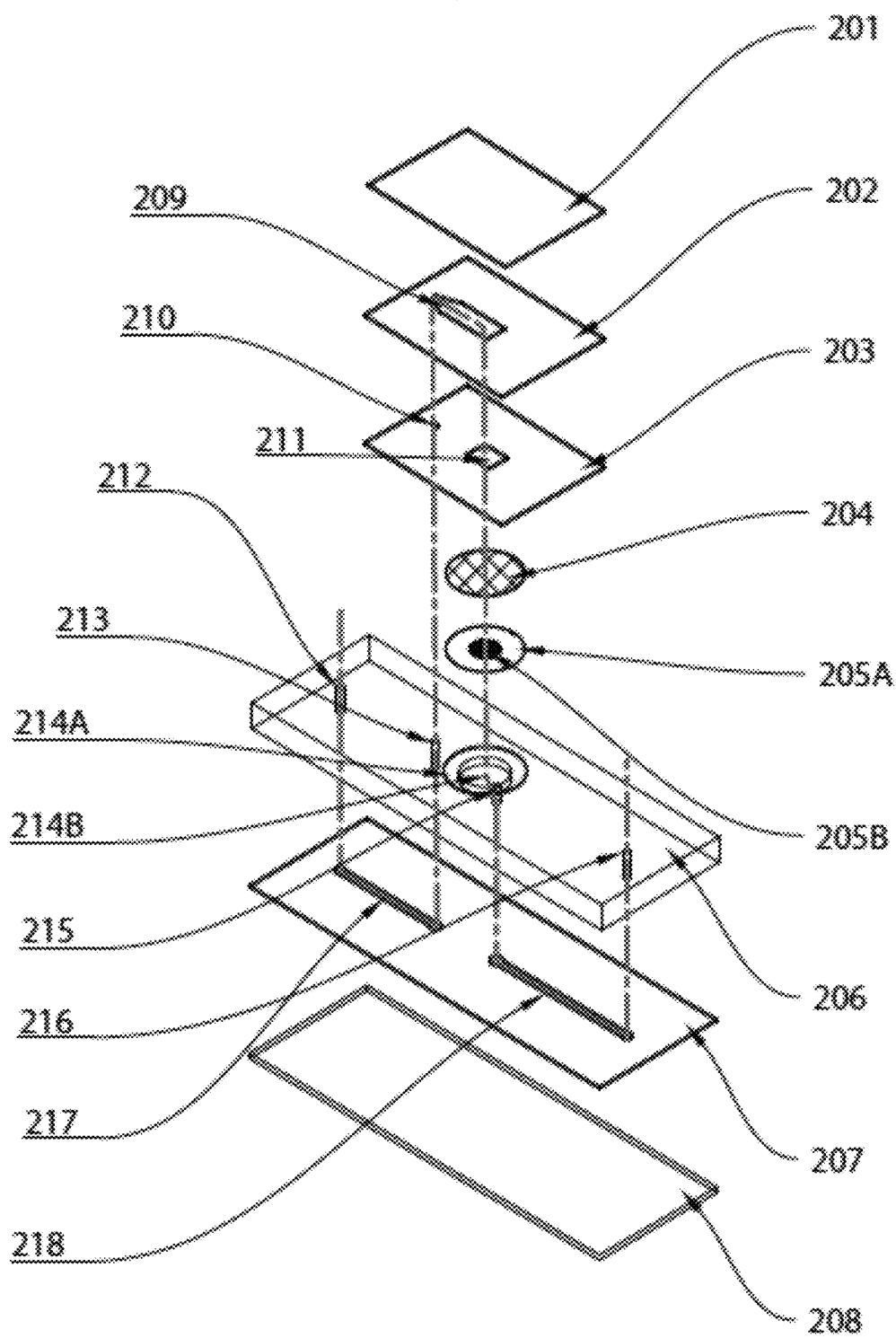
FIG. 2A-C shows a single assay prototype device (SAD) made with various layers.
Figure 2B:
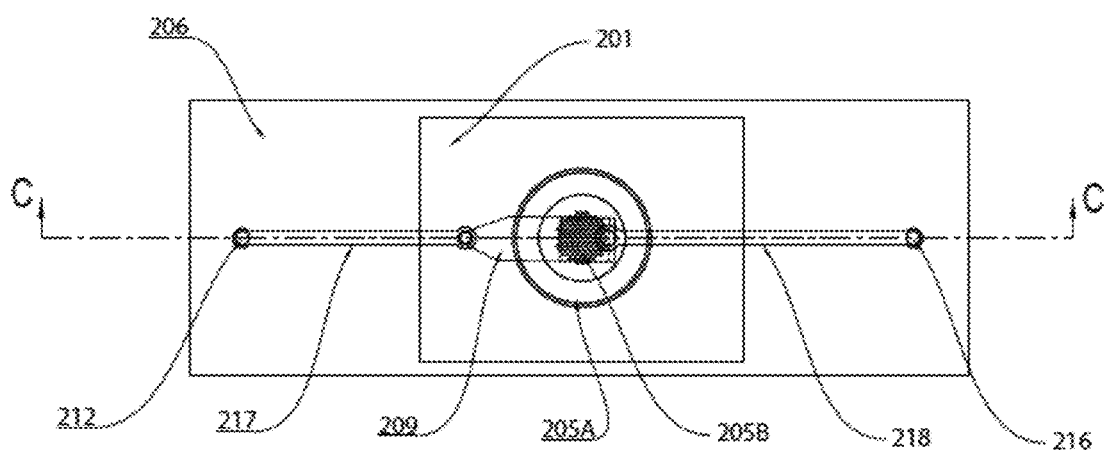
Figure 2C:
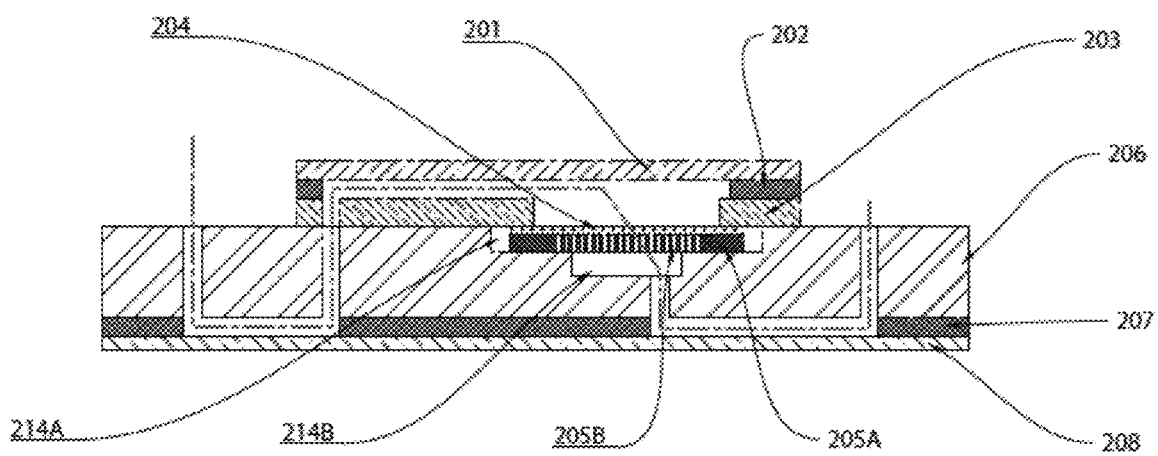

FIG. 2A-C shows a single assay device (SAD) that has been used for large-scale trials in our laboratory setting. It is a multilayer device, where holes are positioned so as to line up in the sandwiched layers. Since the top layer or cover was glass cover slip, fluid entry occurred to the side (inlet) at a lower layer, travelled along a channel in that layer, up through the sandwich to the DSA top layer, laterally in that channel and then down through the sample and out of the device (see dotted line). Such fluid flow prevented leakage, minimized evaporation, and ensured reproducible, reliable results, and yet the device was easy and cost effective to manufacture.

FIG. 2A is useful to illustrate the fluid path as it passes through several planes; specifically, as it passes from the inlet (212) to the bottom inlet channel (217), up through the ascending fluid port (213), across the top fluidic channel (209), down through the porous membrane (204) into the sub-membrane cavity (214B), down through the descending fluid port (215), across the bottom outlet channel (218), and finally up through the outlet port (216). This fundamental fluidic delivery strategy (four changes of direction in fluid inlet) is seen throughout the following figures in various embodiments.

The parts of FIG. 2A-C are as follows:
201. Top optical cover (e.g., cyclic-olefin-copolymer (COC), glass)
202. Top fluidic channel (double-sided adhesive (DSA))
203. Membrane window (single-sided adhesive vinyl)
204. Porous membrane (track-etched polycarbonate)
205. Stainless steel frit-205A. Non-porous region-205B Porous region
206. Acrylic chip (e.g., laser cut/etched, machined, hot embossed, or injection molded)
207. Bottom fluidic channel (DSA)
208. Basement layer (plastic slide), optional
209. Top fluidic channel cutout
210. Ascending fluid port hole
211. Membrane window cutout
212. Inlet port
213. Ascending fluid port
214. Acrylic cavity—214A Frit support cavity—214B Sub-membrane cavity
215. Descending fluid port
216. Outlet port
217. Bottom inlet channel
218. Bottom outlet channel FIG. 3A-E depicts one possible embodiment of the high-throughput, multi-analyte MAD-24 device. The device is composed of 24 repeating units of a single assay region. The fluidic path (4 changes of direction) through a single unit is illustrated with a dashed line through the separate layers.

Figure 3A:
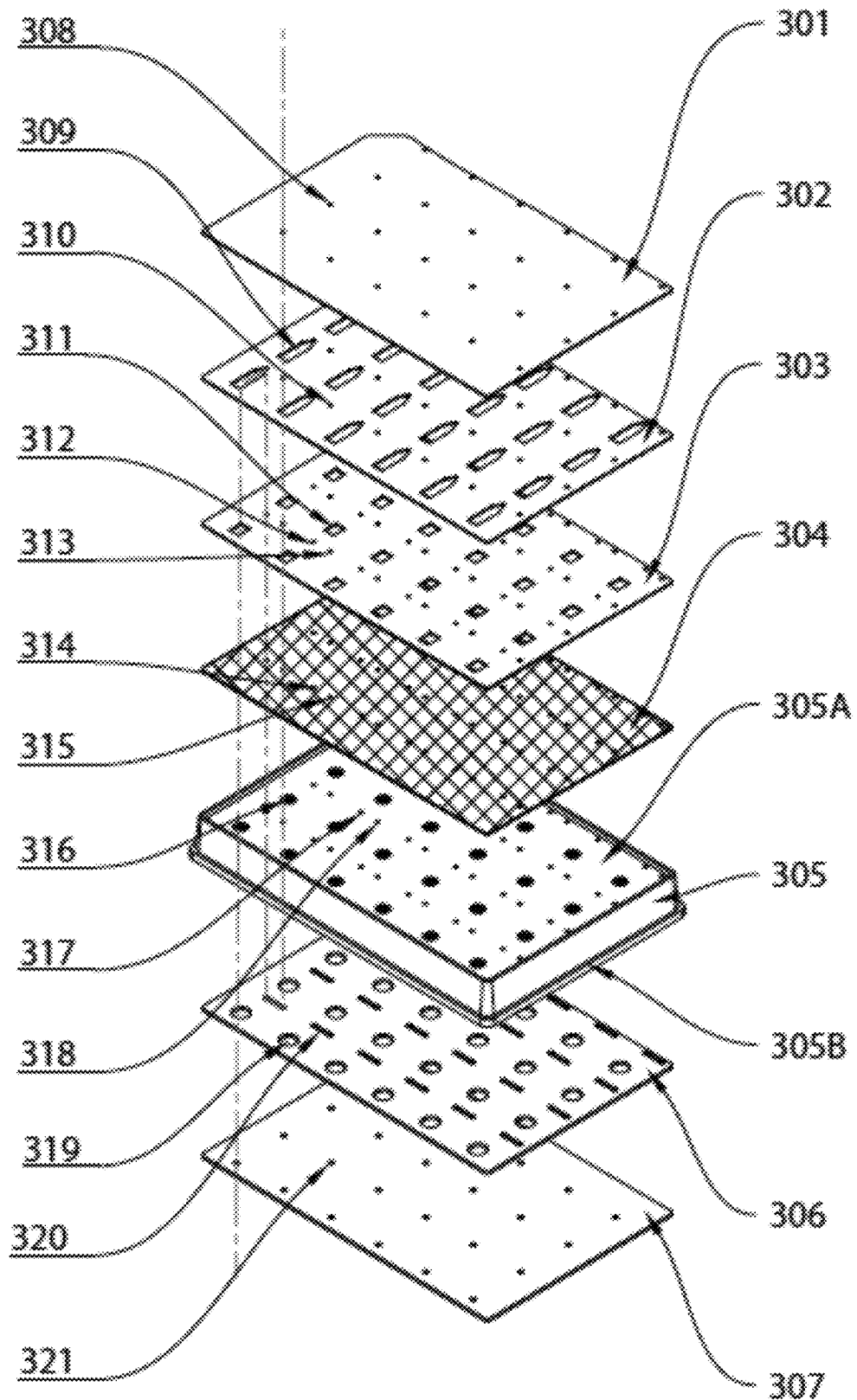
FIG. 3A-C shows a multi assay device (MAD) with 24-assay capability (MAD-24).
Figure 3B:
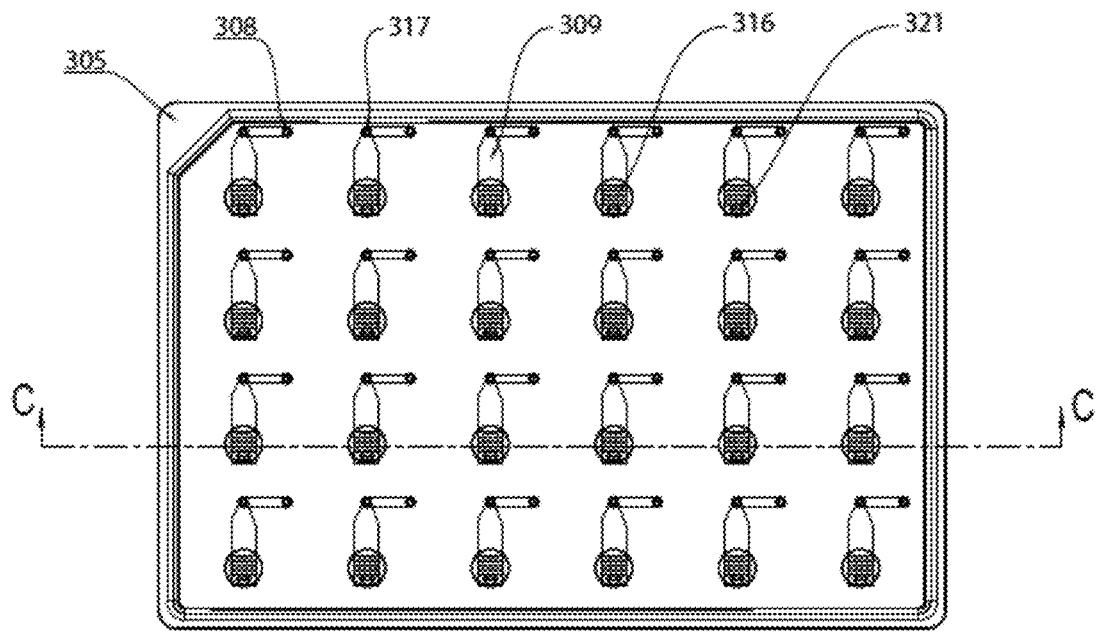

In the exploded view of FIG. 3A, 7 layers are seen, but this is for prototype development only, and the number of layers can be reduced by injection molding both the top and bottom of a given layer, thus combining two layers. Also, double sided adhesive layers can be eliminated when other layering techniques are used, such as RF welding, solvent bonding, heat bonding and the like. These parts have been produced through laser cutting of the various layers, but can be made through other ways (CNC, injection molding, 3D printing, 3D laser, stereolithography (SLA), etc.).

Figure 3C:
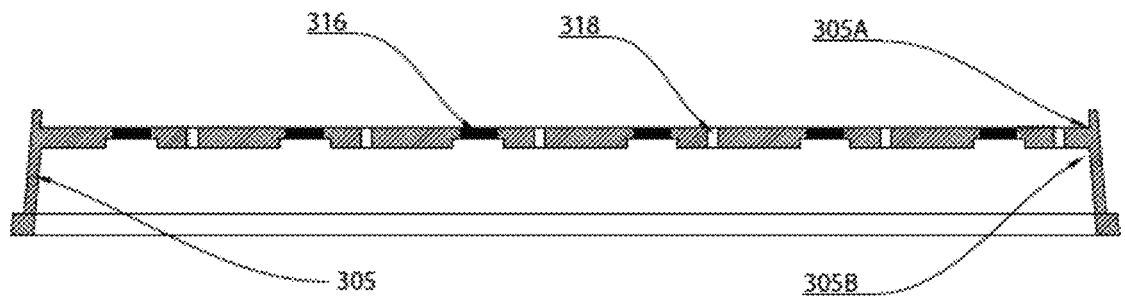
Figure 3D:
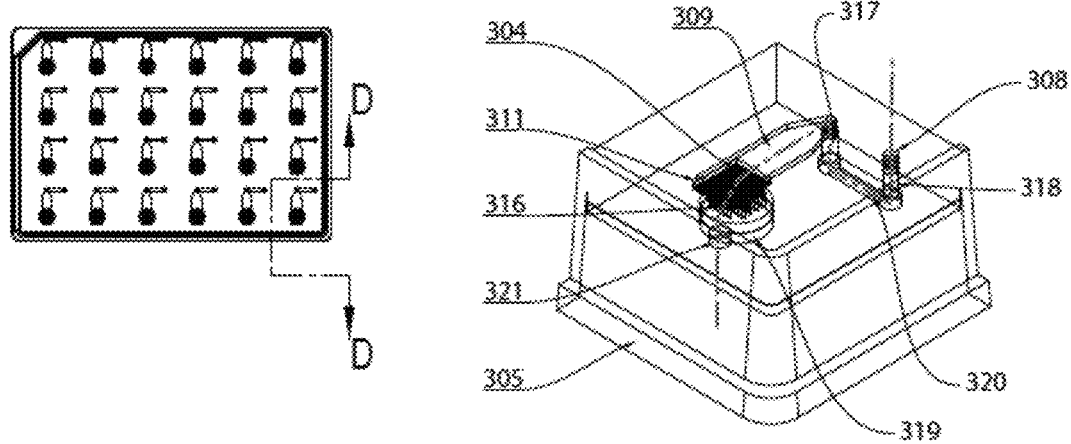
FIG. 3D shows a transparent perspective of a corner reaction chamber showing the fluid pathway in dashed line.
Figure 3E:
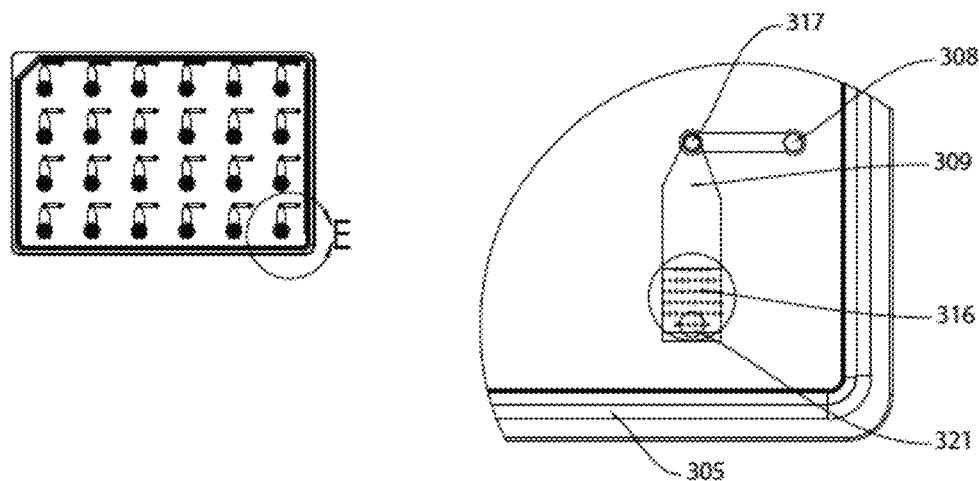
FIG. 3E shows an enlarged top view of a single corner chamber.

FIG. 3C depicts a cross-section view of an injection molded FRIT plate (305) made of acrylic, in order to illustrate the top and bottom pockets that contain the additional layers once fully assembled. These pockets allow for less plastic to be used in injection-molding the device, saving on cost of materials as well as maintaining the overall footprint of the industry-standard microtiter plate. Furthermore, the parts can be sized to tightly fit into these pockets, thus holding the sandwich without the need for fixation means.

Figure 4:
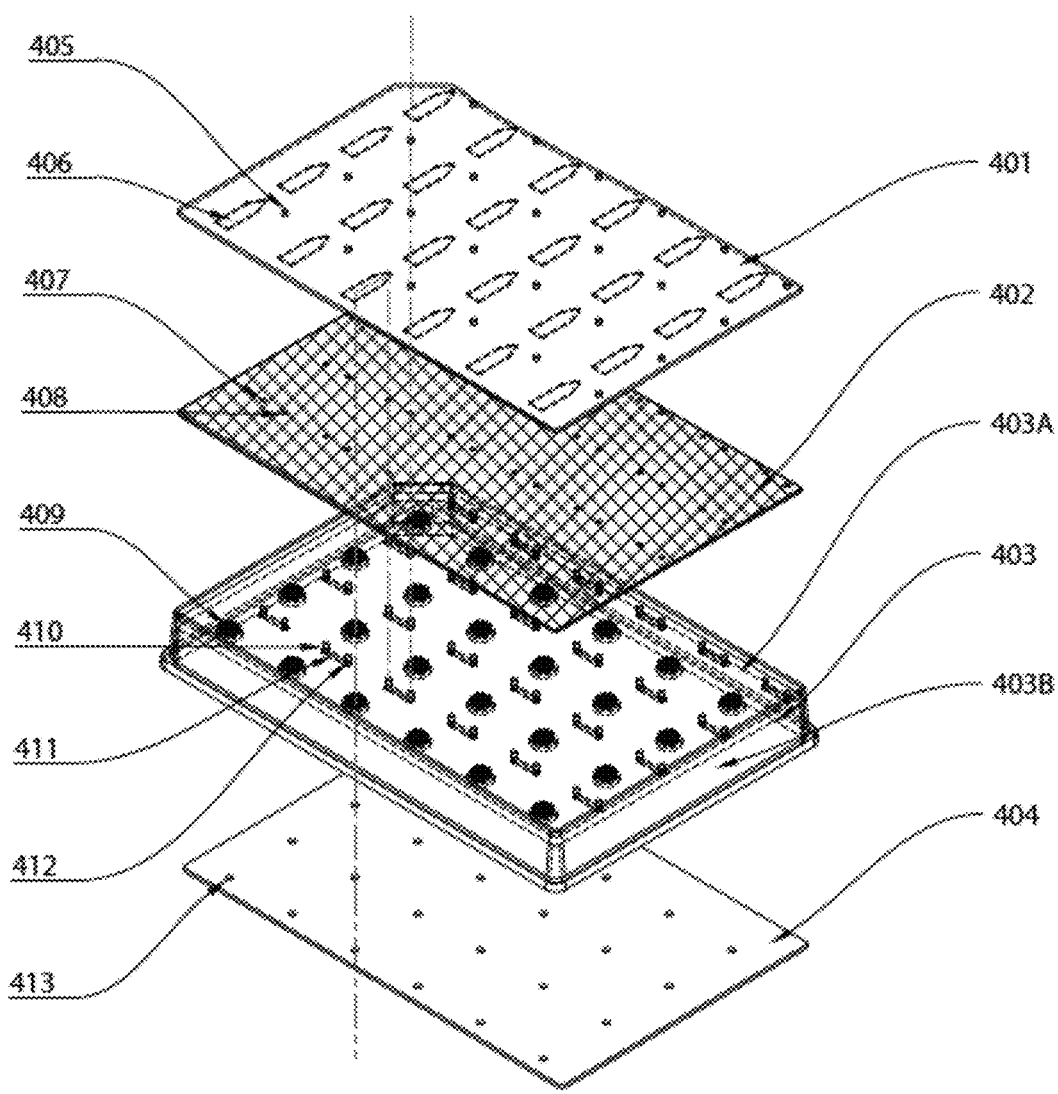
FIG. 4 shows a multi-assay device (MAD-24) made with fewer layers. The fluid pathway is indicated by the dashed line.

The parts of FIG. 3A-E are as follows:
301. Top optical cover (COC)
302. Top fluidic channel (DSA)
303. Membrane cover (single-sided adhesive vinyl)
304. Porous membrane sheet (track-etched polycarbonate)
305. Acrylic plate with embedded Frits (injection molded)
   305A. Top pocket (aligns top layers)
   305B. Bottom pocket (aligns bottom layers)
306. Bottom fluidic channels (DSA)
307. Basement layer (plastic)
308. Inlet hole
309. Top fluidic channel cutout
310. Descending fluid port hole
311. Membrane window cutout
312. Ascending fluid port hole
313. Descending fluid port hole
314. Ascending fluid port hole
315. Descending fluid port hole
316. Embedded frit (monolithic plastic)
317. Ascending fluid port
318. Descending fluid port
319. Sub-membrane cavity
320. Bottom fluid channel
321. Outlet port FIG. 4 shows an alternate embodiment of the multi-analyte device, whereby designs that existed in separate layers are combined strategically through an additional injection-molding step to reduce the overall number of layers and device complexity through assembly. These layers are affixed to each other by any of several methods, such as RF or solvent welding. A dashed line represents the fluid path through the device. The parts of FIG. 4 are:
401. Top cover—injection-molded plastic, top surface is optically clear and flat, bottom surface contains molded top fluidic channels (405)
402. Porous membrane sheet (track-etched polycarbonate)—laminated (heat-staked) to plastic surfaces
403. Injection-molded plate
   403A. Top pocket
   403B. Bottom pocket
404. Basement layer (single-sided adhesive or laminated)
405. Inlet holes
406. Top fluidic channel pocket
407. Ascending fluid port hole
408. Descending fluid port hole
409. Embedded frit
410. Ascending fluid port
411. Bottom fluid channel pocket
412. Descending fluid port
413. Outlet port FIG. 5A-E depicts another alternate embodiment of the multi-analyte device that contains a top fluid manifold layer for reagent dispensing (501). This part can either be designed to operate as a re-usable manifold that interfaces with a disposable assay cartridge (made of the subsequent layered-assembly), or as a composite device where the additional layers are permanently bound, thus negating the need for spring clips (503) or compressible O-rings (502). The fluid path is illustrated as a dashed line.

Figure 5B:
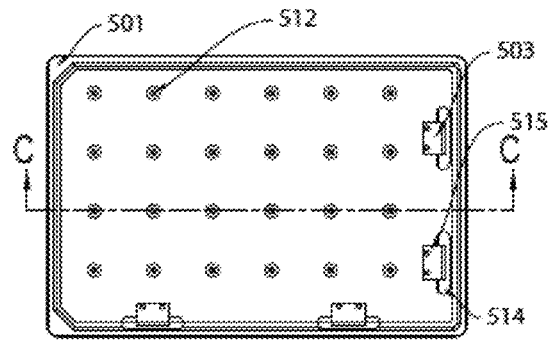
Figure 5C:
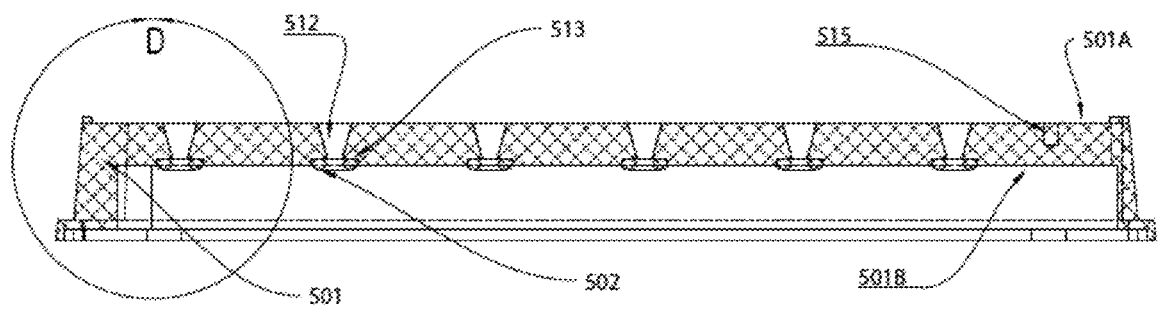

FIG. 5A is an exploded view. FIG. 5B is a top view, illustrating the location of the cross section view in FIG. 5C, which is a cross-section view of the Dosing Manifold (501) illustrates the location and geometry of the parabolic well cavities. For simplicity, the cross-section isolates the dosing manifold without the subsequent layers of the assay device assembly. This figure also denotes the location of the blow-up view for FIG. 5D.

Figure 5D:
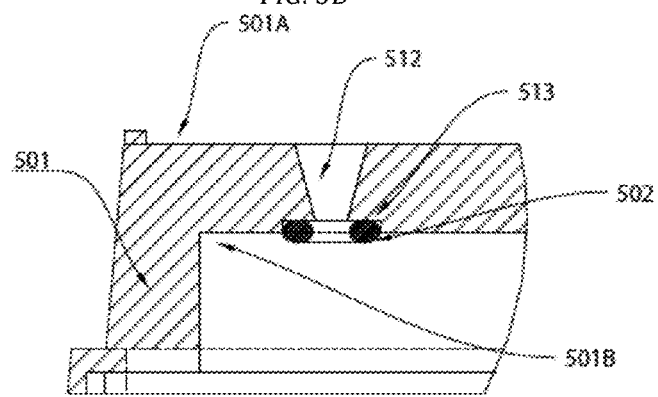

FIG. 5D further illustrates the design of the dosing manifold in an enlarged view. When fully assembled, the assay device layers fit directly inside the bottom cavity (501B). The spring clips (503) act to align the assay cartridge (if designed as a separate assembly) as well as apply a clamping force to allow the compressible O-rings (502) to create a leak-free seal on the inlet port (516).

Figure 5E:
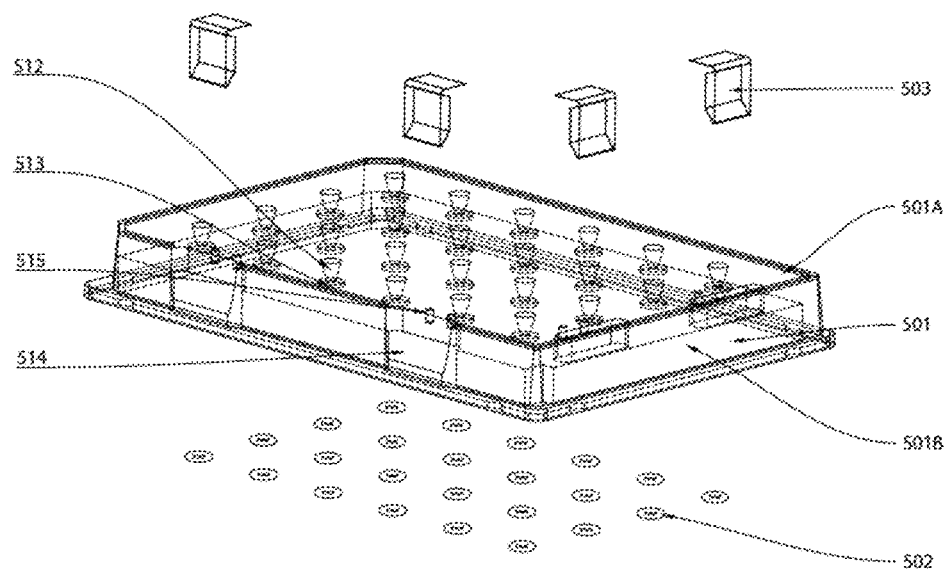

FIG. 5E is an isometric exploded view that depicts the dosing manifold in another orientation in order to obtain a more three-dimensional perspective of the arrangement of the dosing wells. The wells are designed to have the same height and planar location as wells on a 96-well plate so that a robotic liquid handling robot could perform the assays without manual assistance.

The parts in FIG. 5 are:
501. Dosing manifold (injection-molded plastic)
   501A. Top pocket
   501B. Bottom pocket
502. Compressible silicone O-rings
503. Stainless steel spring clips
504. Top optical cover (COC)
505. Top fluidic channel (DSA)
506. Membrane cover (single-sided adhesive vinyl)
507. Porous membrane sheet (track-etched polycarbonate)
508. Acrylic plate with embedded Frit (injection molded)
509. Bottom fluidic channels (DSA)
510. Basement layer (plastic)
511. Absorbent waste pad
512. Dosing well cavity
513. O-ring pocket
514. Spring clip pocket
515. Faster hole for attaching spring clips
516. Inlet hole
517. Descending fluid port hole
518. Top fluidic channel cutout
519. Descending fluid port hole
520. Membrane window cutout
521. Descending fluid port hole
522. Ascending fluid port hole
523. Descending fluid port
524. Embedded frit (monolithic plastic)
525. Ascending fluid port
526. Bottom inlet channel
527. Bottom outlet channel
528. Waste cutout FIG. 6A depicts a three assay device MAD-3 that operates without the need for external pumping by using the wicking force of an absorbent waste pad to drive fluid flow. This exploded view shows the individual layers and illustrates the fluid path with a dashed line. This device is part of an additional assembly that is illustrated in FIG. 6D. Note the vertical absorbent pads, allowing separate pads and thus separate control of the three reaction chambers.

Figure 6B:
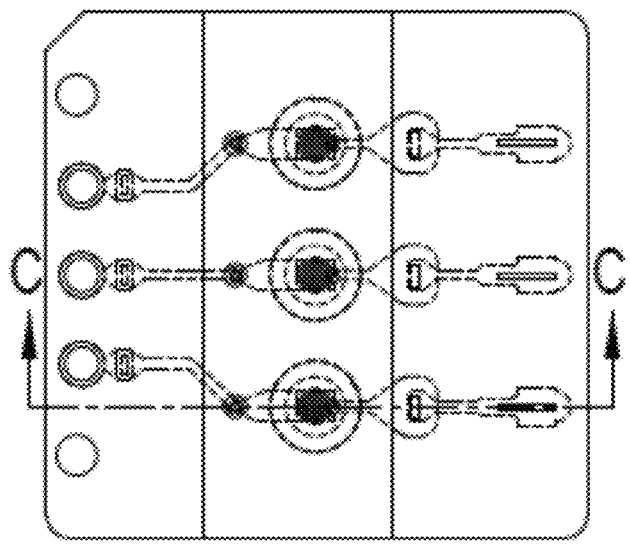
Figure 6C:
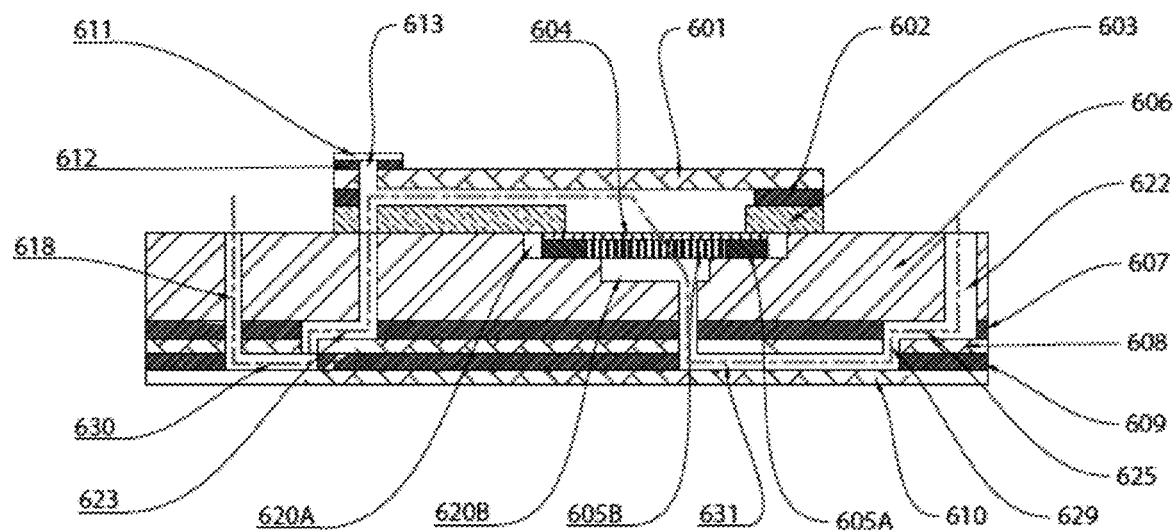
Figure 6D:
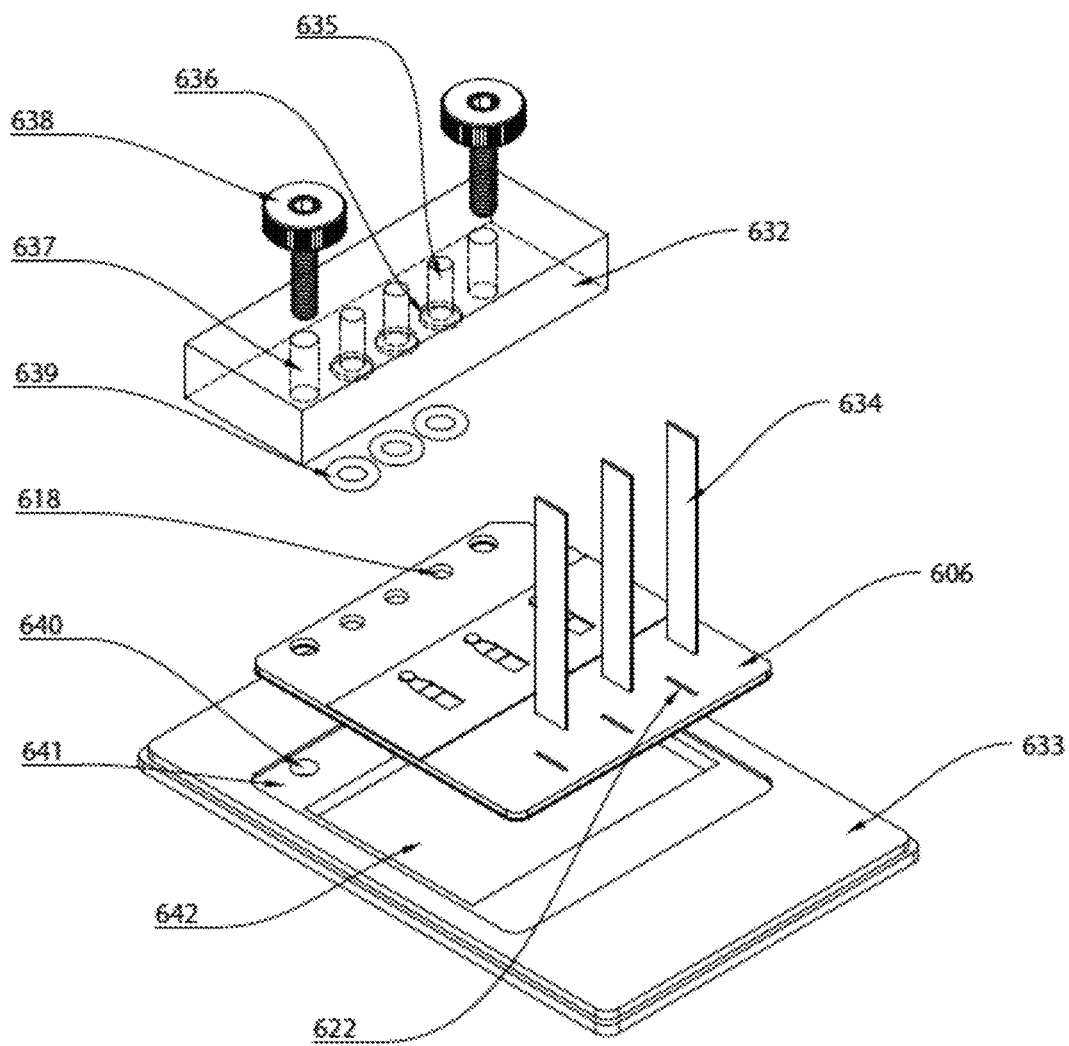
FIG. 6D is a perspective view of the device as assembled together with additional parts.

FIG. 6B depicts the passively-driven 3-assay device from FIG. 6A in a top view, illustrating the location of the cross sectional view in FIG. 6C. FIG. 6C illustrates the fluidic path (dashed line) as well as the laminate structure of the device once assembled. FIG. 6D shows the additional assembly components to perform an assay on the sub-assembly device depicted in FIG. 6A.

Preceding operation of the device, the fluidic channel path must first be primed with buffer until the fluid reaches the outlet so that assay initiation will begin as soon as the first absorbent pad (634) is inserted into the outlet pad holder (622). The inclusion of the two passive valve holes (626, 629) regulates the fluid during priming so that a user receives visual feedback of when to stop channel priming.

The parts in FIG. 6 are listed as follows:
601. Top optical cover (COP)
602. Top fluidic channels (DSA)
603. Membrane window (single-sided adhesive vinyl)
604. Porous membrane (track-etched polycarbonate)
605. Stainless steel frit
   605A. Non-porous region
   605B. Porous region
606. Acrylic card (laser cut/etched, machined, hot embossed, injection molded)
607. Accessory fluid channels (DSA)
608. Passive fluid valves (PET)
609. Bottom fluidic channels (DSA)
610. Basement layer (plastic)
611. Air-venting hydrophobic membranes
612. DSA gasket
613. Vent holes
614. Top fluidic channel cutout
615. Ascending fluid port hole
616. Membrane window cutout
617. Fastener holes
618. Inlet ports
619. Ascending fluid port
620. Acrylic cavity
   620A. Frit support cavity
   620B. Sub-membrane cavity
621. Descending fluid port
622. Absorbent pad holder (cutout)
623. Inlet accessory fluid channel
624. Descending fluid port hole
625. Outlet accessory fluid channel
626. Inlet passive valve hole
627. Ascending fluid port hole
628. Descending fluid port hole
629. Outlet passive valve hole
630. Bottom inlet channel
631. Bottom outlet channel
632. Fluid dosing manifold
633. Bottom, card-supporting plate
634. Absorbent pads (cellulose)
635. Fluid dosing well
636. O-ring pocket
637. Fastener holes
638. Thumb-screw fasteners
639. Compressible O-rings
640. Threaded fastener holes
641. Assay card pocket
642. Bottom plate hole FIG. 7A depicts an embodiment of an automated, passive fluid pumping scheme in a 12-analyte device (MAD-12) in an exploded view to illustrate the individual layers. The overall functionality as described herein is maintained, but with the important addition of a pierce-able foil barrier (710) between the priming buffer and the absorbent pad sink (711). The foil barrier can be punctured with minimal force from the end of a disposable pipette tip.

The location of the inlet well and the foil barrier are strategically designed to occupy x-y positions of wells from a standard 96-well microtiter plate. From this compatibility, fully automated assays can be performed from sample preparation, reagent addition and barrier puncture. For simplicity in labeling, redundant features present in multiple layers were omitted. The dashed line represents the fluid path through a single assay region on the 12-analyte device. To better isolate the single assay-unit depicted with the dashed line, the features that compose the single unit are outlined in black while all other features are in gray.

Figure 7B:
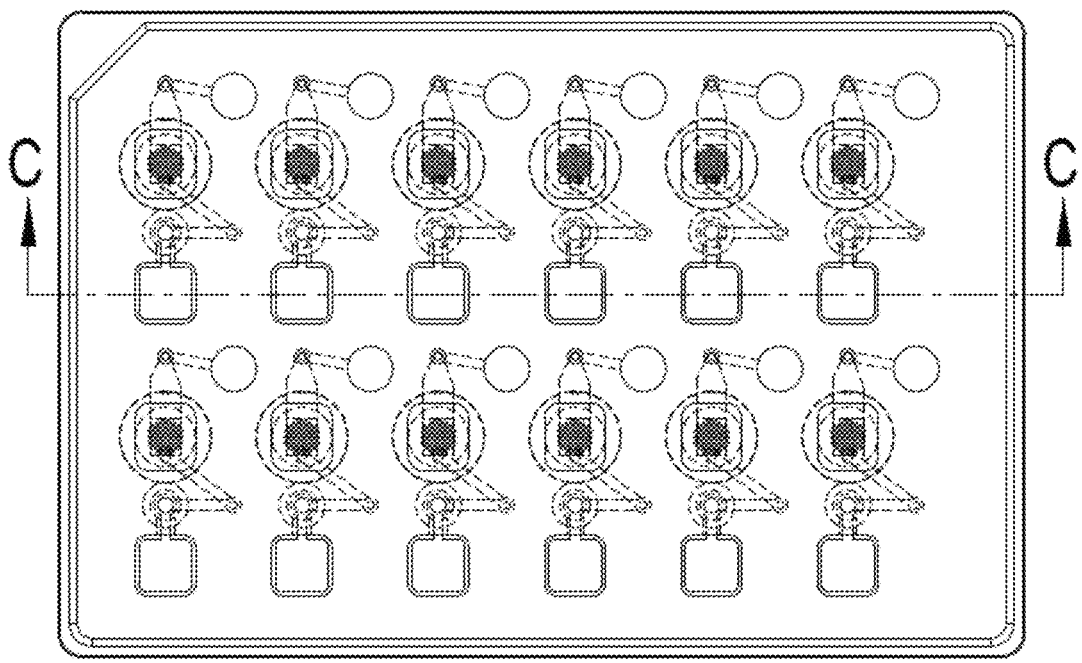
Figure 7C:
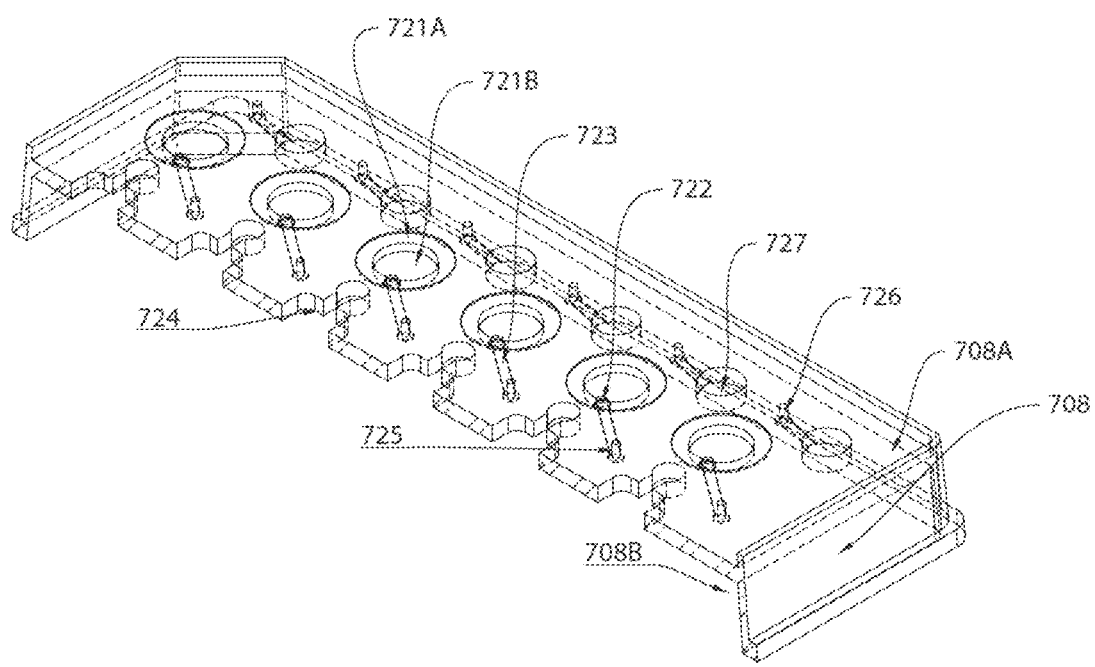

FIG. 7B depicts the device of 7A in a top view. The line C-C represents the location of the cut away perspective view in 7C. This isometric view illustrates the depth of the membrane cavities, the pockets that form the microfluidic channels on the bottom surface of the part, and the through-holes that interface with the different fluidic layers.

Figure 7D:
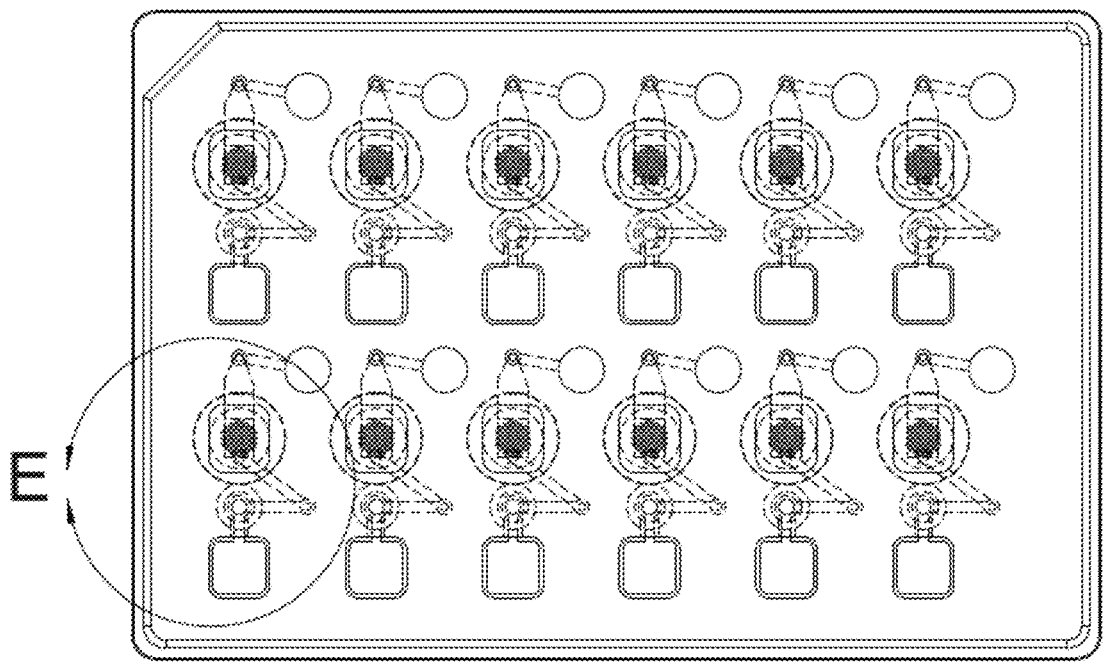
Figure 7E:
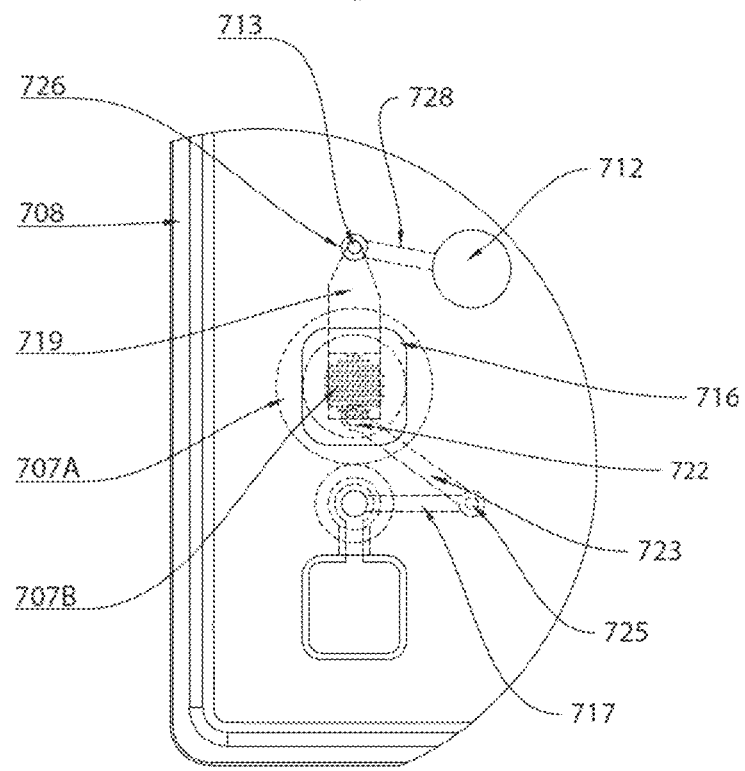
Figure 7F:
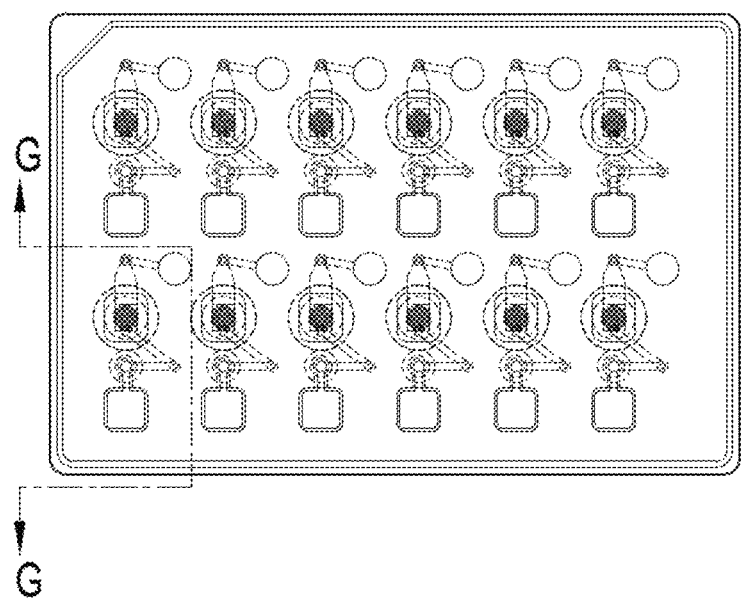
Figure 7G:
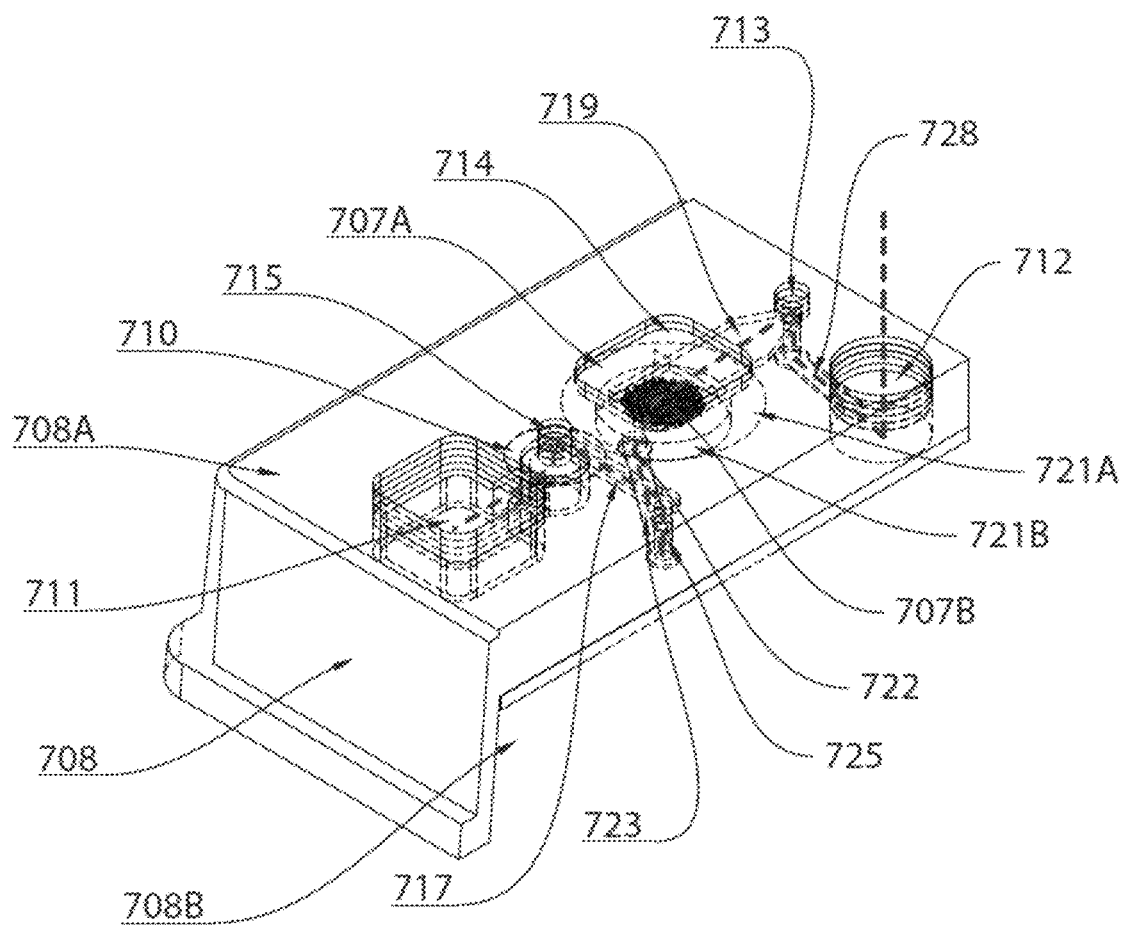

FIG. 7D shows a top view of the assembled device, where the circle locates the blow-up view for FIG. 7E, which is a top view enlargement of a single assay-unit of the 12-analyte device. FIG. 7F is another top view of the assembled device, the dashed line G-G locates the cutout view for FIG. 7G, which is an isometric cutout view of a single assay-unit to better illustrate the complex fluid path. The dashed line represents the fluid path as it passes from the inlet well (712) to the bottom embedded microchannel (728) to the ascending inlet port (713), across the top membrane channel (719), down through the porous membrane (706), to the descending fluid port (722), to the bottom outlet channel (723), to the accessory channel ascending port (725), across the accessory fluidic channel (717) to the foil puncture port (715), and ultimately through to the absorbent pad beneath the foil barrier (716). When the device is primed prior to the start of the assay, the fluidic system is saturated with buffer up until the foil barrier. Once this barrier is punctured with the end of a pipette tip, the fluid immediately contacts the absorbent pad, and the passive pumping caused by the wicking motion and pressure differential of the absorbent pad starts the assay.

The parts in FIG. 7 are:
701. Top cover (PET)
702. Top accessory microchannel (DSA)
703. Top optical cover (COC)
704. Top membrane channel (DSA)
705. Membrane window (vinyl)
706. Porous membrane (track-etched polycarbonate)
707. Stainless steel frit
　707A. Non-porous edge
　707B. Porous center
708. Injection molded assay plate
　708A. Top pocket
　708B. Bottom pocket
709. Basement layer (plastic, single-sided adhesive or laminate)
710. Aluminum foil barriers
711. Absorbent cellulose pads
712. Inlet well hole
713. Ascending inlet fluid port hole
714. Membrane window cutout
715. Pipette adapter for foil puncture port
716. Absorbent pad window cutout
717. Top accessory microchannel
718. Accessory channel ascending fluid port hole
719. Top membrane channel
720. Membrane window cutout
721. Acrylic cavity
　721A. Frit support cavity
　721B. Sub-membrane cavity
722. Descending fluid port
723. Embedded bottom outlet channel
724. Absorbent pad holder cutout
725. Accessory channel ascending fluid port
726. Ascending inlet fluid port
727. Inlet well
728. Embedded bottom inlet channel The present invention is exemplified with respect to 3, 6, 12, or 24 multi-sample cartridges made by laser etching plastic sheets and combining same in layers to create the microfluidics. However, this is exemplary only, and the invention can be broadly applied to various materials and methods. In particular, the number of assays can be increased or decreased, although it is preferred to follow standard plate formats. In addition, 3D or injection molding methods of manufacture may eliminate the use of several layers.

The following references are incorporated by reference in their entirety.

Weigum, S. E., et al., Lab on a Chip 2007, 7, 995-1003.
Weigum, S. E., et al., Cancer Prevention Research 2010, 3, 518-528.
Weigum, S. E., et al., Oral Oncology 2009, 3, 111-111.
U.S. Pat. No. 8,377,398 METHODS AND COMPOSITIONS RELATED TO DETERMINATION AND USE OF WHITE BLOOD CELL COUNTS
WO2007134191 DETECTING MULTIPLE TYPES OF LEUKOCYTES
WO2007134189 DETECTING TUMOR BIOMARKER IN ORAL CANCER
US2008050830 DETECTING MULTIPLE TYPES OF LEUKOCYTES
WO2005090983 MEMBRANE ASSAY SYSTEM INCLUDING PRELOADED PARTICLES
WO2005085854—PARTICLE ON MEMBRANE ASSAY SYSTEM
US2006234209—A MICROCHIP-BASED SYSTEM FOR HIV DIAGNOSTICS
WO2012065025—PROSTATE CANCER POINT OF CARE DIAGNOSTICS
WO2012065117—ORAL CANCER POINT OF CARE DIAGNOSTICS
61/484,492, filed May 10, 2011
61/558,165, filed Nov. 10, 2011
http://openwetware.org/images/4/43/Microplate-dimensions.pdf

The invention claimed is:

1. A bionanochip cartridge comprising:
a) a substrate having an exterior footprint the width and length and shape of a standard microtiter plate; and,
b) said substrate having a plurality of sample analysis arrangements therein, each sample analysis arrangement having:
　i) a top loading inlet port fluidly connected to a reaction chamber that is laterally spaced from said inlet port;
　ii) an indirect fluid pathway connecting said inlet port and said reaction chamber;
　iii) said reaction chamber having a transparent cover overhead allowing visual inspection of said reaction chamber from overhead;
　iv) said reaction chamber having a porous base; and,
　v) said reaction chamber fluidly connected under said porous base to an outlet port.

2. The bionanochip cartridge of claim 1, wherein said indirect fluidic pathway has 4 changes of direction before reaching said reaction chamber.

3. The bionanochip cartridge of claim 1, wherein said indirect fluidic pathway has 3 changes of direction before reaching said reaction chamber.

4. The bionanochip cartridge of claim 1, wherein said indirect fluidic pathway has 2 or 1 changes of direction before reaching said reaction chamber.

5. The bionanochip cartridge of claim 1, wherein said indirect fluidic pathway begins at a top of said cartridge, proceeds to below said reaction chamber, then laterally, then to above said reaction chamber, then laterally, and then down to said reaction chamber.

6. The bionanochip cartridge of claim 1, further comprising a plurality of outlet pathways beneath said membrane, said outlet pathways fluidly connected to said outlet port.

7. The bionanochip cartridge of claim 1, wherein said porous base comprises a membrane.

8. The bionanochip cartridge of claim 1, wherein said porous base comprises a membrane and a porous frit beneath said membrane.

9. The bionanochip cartridge of claim 1, wherein said fluidic pathway has a hydrophilic fluid contacting surface.

10. The bionanochip cartridge of claim 1, further comprising an absorbent pad below said substrate and fluidly connected to said outlet port.

11. The bionanochip cartridge of claim 1, wherein said outlet port is directly below said reaction chamber.

12. The bionanochip cartridge of claim 1, wherein said substrate is comprised of at least a transparent cover layer over an inlet layer over a reaction chamber layer over an outlet layer, each of said layers affixed to an adjacent layer in a fluid tight manner.

13. The bionanochip cartridge of claim 1, wherein said substrate is comprised of at least an inlet layer over a transparent cover layer over a reaction chamber layer over an outlet layer, each of said layers affixed to an adjacent layer in a fluid tight manner.

14. The bionanochip cartridge of claim 1, wherein said substrate is comprised of at least an inlet layer, a transparent cover layer, a reaction chamber layer, and an outlet layer, each of said layers affixed to an adjacent layer in a fluid tight manner.

15. The bionanochip cartridge of claim 14, wherein said transparent cover layer is an uppermost layer.

16. The bionanochip cartridge of claim 14, wherein said transparent cover layer is an intermediate layer.

17. The bionanochip cartridge of claim 14, wherein at least one of said layers contains at least one pocket on a top or bottom surface thereof for tightly receiving additional layers.

18. The bionanochip cartridge of claim 14, wherein an uppermost layer has an exterior the size and shape of a microtiter plate and has a pocket on a bottom surface thereof for tightly holding additional layers.

19. The bionanochip cartridge of claim 14, wherein a middle layer has an exterior the size and shape of a microtiter plate and has pockets on a bottom surface thereof and a top surface thereof for tightly holding additional layers.

20. The bionanochip cartridge of claim 19, said middle layer having one or more pockets to receive one or more frits.

21. The bionanochip cartridge of claim 1, further comprising a bottom layer comprising an absorbent material.

22. The bionanochip cartridge of claim 14, further comprising a bottom layer comprising an absorbent material sized to absorb all fluid from an assay.

23. The bionanochip cartridge of claim 14, further comprising an impermeable layer above a bottom layer comprising an absorbent material and wherein a hole is provided through said bionanochip cartridge such a that a user can penetrate said impermeable layer through said hole.

24. A bionanochip cartridge comprising:
   a) a substrate made of layers held in leak proof juxtaposition and having an exterior footprint the width and length and shape of a standard microtiter plate; and,
   b) said substrate having a plurality of sample analysis arrangements therein, each sample analysis arrangement having:
      i) a top loading inlet port fluidly connected to a reaction chamber that is laterally spaced from said inlet port;
      ii) an indirect fluidic pathway having at least 2 changes of direction connecting said inlet port and said reaction chamber;
      iii) said reaction chamber having a transparent cover overhead allowing visual inspection of said reaction chamber from overhead;
      iv) said reaction chamber having a porous base;
      v) said porous base fluidly connected to a outlet port; and,
      vi) an absorbent pad below said outlet port.

25. The bionanochip cartridge of claim 24, further comprising a plurality of outlet pathways beneath said membrane, said outlet pathways fluidly connected to said outlet port.

26. The bionanochip cartridge of claim 24, said porous base comprising a membrane for catching cells or a membrane for catching cells with a fit thereunder.

27. The bionanochip cartridge of claim 24, said porous base comprising an agarose pad or agarose bead.

28. The bionanochip cartridge of claim 27, said agarose having one or more antibodies conjugated thereto.

29. The bionanochip cartridge of claim 24, wherein an uppermost layer has an exterior the size and shape of a microtiter plate and has a pocket on a bottom surface thereof for tightly holding additional layers.

30. The bionanochip cartridge of claim 24, wherein a middle layer has an exterior the size and shape of a microtiter plate and has a bottom pocket on a bottom surface thereof and a top pocket on a top surface thereof for tightly holding additional layers.

31. The bionanochip cartridge of claim 24, the plurality of sample analysis arrangements reflecting an arrangement of wells on a standard microtiter plate.

* * * * *